(12) United States Patent
Kucharczyk

(10) Patent No.: US 7,049,070 B2
(45) Date of Patent: May 23, 2006

(54) MATERIALS AND METHODS FOR DETECTION AND CHARACTERIZATION OF NUCLEIC ACID SEQUENCE VARIABILITY

(76) Inventor: Krzysztof Kucharczyk, ul. Dzieci Warszawy 31/20, 02-495 Warsaw (PL)

( * ) Notice: Subject to any disclaimer, the term of this patent is extended or adjusted under 35 U.S.C. 154(b) by 0 days.

(21) Appl. No.: 10/212,486

(22) Filed: Aug. 6, 2002

(65) Prior Publication Data

US 2003/0077631 A1 Apr. 24, 2003

Related U.S. Application Data

(63) Continuation-in-part of application No. PCT/PL01/00012, filed on Feb. 7, 2001.

(51) Int. Cl.
*C07H 21/04* (2006.01)
*C12Q 1/68* (2006.01)
(52) U.S. Cl. .................. 435/6; 435/91.1; 435/91.2; 536/23.1
(58) Field of Classification Search ............... 435/6, 435/91.1, 91.2; 536/23.1
See application file for complete search history.

(56) References Cited

U.S. PATENT DOCUMENTS 6,153,811 A * 11/2000 Lowe et al. ............. 800/278
6,287,441 B1 * 9/2001 Liu et al. ................. 204/461

OTHER PUBLICATIONS

Chen et al. (Nucleic acids Research, vol. 23, No. 21, pp. 4524-4525, 1995).*
Sugano et al. (Electrophoresis, vol. 16, pp. 8-10, 1995).*
Rubben et al. (Eur. J. of Epidemiology, vol. 11, pp. 501-506 1995).*
Wallace (Laboratory methods for the detection of mutations and polymorphisms in DNA, 2000, pp. 79-94).*

* cited by examiner

*Primary Examiner*—Jeanine A. Goldberg
(74) *Attorney, Agent, or Firm*—Gary J. Gershik; Cooper & Dunham LLP

(57) ABSTRACT

A method for influencing the separation mobility of single stranded nucleic acids in native conditions is disclosed. Temperature changes during the separation of single stranded nucleic acids under native conditions are used as the basis of a novel method of detection of specific nucleic acid sequences.

62 Claims, 11 Drawing Sheets

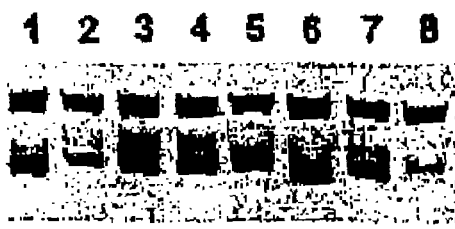
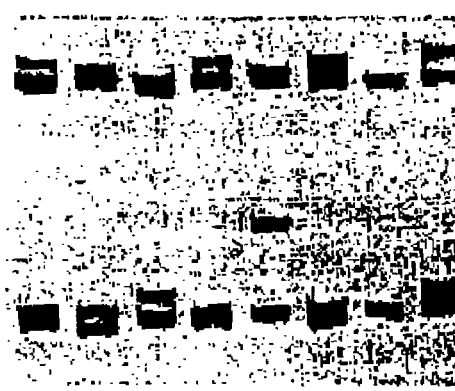
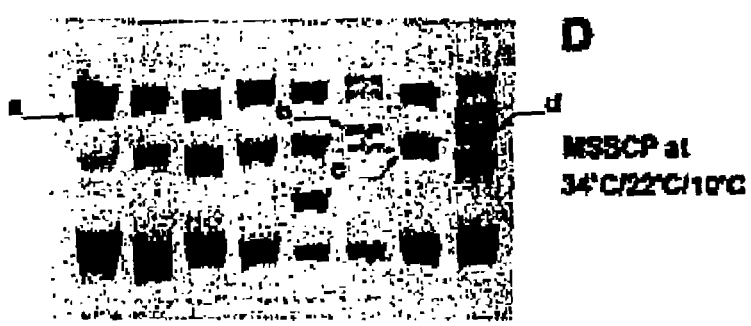
FIG. 6A
FIG. 6B
FIG. 6C
FIG. 6D

| Lane no. in Fig. 6D | Band | Sequence | | Amino acid mutation | Remarks |
|---|---|---|---|---|---|
| | | Whole Sample | Eluted Band | | |
| 1 | a | G782A | G782A | R261Q | Homozygotic |
| 6 | b | G814G/T | G814G/T | G272X | Heterozygotic 1:1 |
| | | G898G/T | G898G/T | A300S | |
| 7 | c | wt | wt | wt | Homozygotic |
| 8 | d | C781T | C781T | R261X | Homozygotic |
| | | T734C | T734C | V245A | |

FIG. 6E

Lanes:

A,E - mutation Arg3500Gln
B,F - mutation Thr3492Ile
C,G - mutation Arg3551Cys
D,H - Wild Type

SEQUENCE LISTING

<160> NUMBER OF SEQ ID NOS: 8

<210> SEQ ID NO 1
<211> LENGTH: 20
<212> TYPE: DNA
<213> ORGANISM: Artificial sequence
<220> FEATURE:
<223> OTHER INFORMATION: oligonucleotide primer

<400> SEQUENCE: 1
atttccttac tgcctcttgc                                                    20

<210> SEQ ID NO 2
<211> LENGTH: 20
<212> TYPE: DNA
<213> ORGANISM: Artificial sequence
<220> FEATURE:
<223> OTHER INFORMATION: oligonucleotide primer

<400> SEQUENCE: 2
aagtgaatct gaggcataac                                                    20

<210> SEQ ID NO 3
<211> LENGTH: 21
<212> TYPE: DNA
<213> ORGANISM: Artificial sequence
<220> FEATURE:
<223> OTHER INFORMATION: oligonucleotide primer

<400> SEQUENCE: 3
tgcctctgac tcagtggtga t                                                  21

<210> SEQ ID NO 4
<211> LENGTH: 22
<212> TYPE: DNA
<213> ORGANISM: Artificial sequence
<220> FEATURE:
<223> OTHER INFORMATION: oligonucleotide primer

<400> SEQUENCE: 4
cccaaacctc attcttgcag ca                                                 22

<210> SEQ ID NO 5
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 5
tggggatccc gtatgatacc cgctgctttg a                                       31

<210> SEQ ID NO 6
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 6
gcggaattcc tggtcatagc ctccgtgaa                                          29

<210> SEQ ID NO 7
<211> LENGTH: 24

```
-continued

<212> TYPE: DNA
<213> ORGANISM: Artificial Sequence
<220> FEATURE:
<223> OTHER INFORMATION: oligonucleotide primer

<400> SEQUENCE: 7
ctcaaccgtc actgagagag acat                                              24

<210> SEQ ID NO 8
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 8
gctctcaggt tccgctcgtc ctcc                                              24
```

MATERIALS AND METHODS FOR DETECTION AND CHARACTERIZATION OF NUCLEIC ACID SEQUENCE VARIABILITY

CROSS-REFERENCE TO RELATED APPLICATIONS

This application is a continuation-in-part of International Application No. PCT/PL01/00012, with an international filing date of Feb. 7, 2001. The content of all the aforesaid application is relied upon and incorporated by reference in its entirety.

BACKGROUND OF THE INVENTION

1. Field of the Invention

The present invention relates to materials and methods for rapid detection and characterization of nucleic acid sequences and sequence variability. The present invention relates to means for changing the separation mobility of single stranded nucleic acids in a temperature dependent manner. Changes in separation mobility are used to detect known and unknown single base changes in nucleic acids.

2. Background Art

Genetic variability observed between specimens of any species is the result of polymorphism developed during biological evolution and from spontaneous mutations accumulated during the lifespan of individuals. Establishing the correlation between genetic variations, the environment, and the phenotype of an organism (or a population) could provide vital information for understanding the basic mechanism of life.

One of the most often observed polymorphisms is a Single Nucleotide Polymorphism (SNP) where a single base pair distinction exists in the sequence of a nucleic acid stranded compared to the most prevalently found (wild type) nucleic acid strand. When a SNP occurs in the gene coding for a structural protein or its regulating region, the polymorphic locus may influence the function of the encoded protein and cells which express the protein, in addition to affecting the organismal phenotype.

In most cases, the observed phenotype in higher organisms is the result of the interaction between several gene products. The phenotype resulting from a mutation or SNP at a first locus may be offset, or compensated for by mutations at a second locus. As the compensation/adjustment mechanism influences the final phenotype, the polymorphic pattern and mutation frequency correlating to any phenotype might only be slightly different in an affected group compared to a control group. To establish such correlations, genome-population-wide association studies are usually required.

Since such studies could significantly improve the quality of human life, for example, by introducing DNA-based diagnostics and pharmacogenomics practice into hospital routines, establishing a reliable methodology of DNA mutation and polymorphism analysis on the genome-population-wide scale is strongly needed. Despite the fact that sequencing of DNA becomes more and more a routine methodology, none of the currently existing technical methods for genetic sequence variation detection could be applied to, e.g., human genome-population-wide genetic surveys in an acceptable time and cost scale.

At present, at least three steps can be identified for the mutation/SNP detection process. In the first step, the regions/genes of the genome to be analyzed must first be selected. In the second step, screening for the presence of mutations/SNP in the selected genes/regions is conducted. In the last step sequencing of selected samples may be performed. The accuracy of the mutation/SNPs detection process depends on the amount of target nucleic acid (NA) in the analyzed sample. Several standard methods are available for purifying nucleic acids from the starting material, in addition to the wide selection of commercial kits available for nucleic acid purification.

When a sufficient amount of the isolated target nucleic acid is acquired, "direct mutation detection" methods can be applied to detect nucleic acid. Methods for "direct detection" of specific sequences in nucleic acids are mostly based on the NA/NA hybridization (e.g, Branched DNA method bDNA-Urdea et al., *Gene* 61:253–264 (1987) or protein/NA interaction (Restriction Fragment Length Polymorphism-RFLP)).

However, when the amount of the target nucleic acid in the analyzed sample is too low for direct analysis, an amplification step of selected nucleic acid fragments is necessary. The most popular method used for the amplification of target nucleic acid fragments is Polymerase Chain Reaction (PCR) as described in U.S. Pat. Nos. 4,683,195 and 4,683,202 to Mullis et al. The process comprises treating separate complementary strands of the target nucleic acid with a molar excess of two oligonucleotide primers; extending the primers with thermostable DNA polymerase to form complementary primer extension products which act as templates for synthesizing the desired nucleic acid sequence; and detecting the amplified sequence. The steps of the reaction may be carried out stepwise, or simultaneously, and can be repeated as often as desired. Other methods used for nucleic acid amplification include:

Ligase Chain Reaction (LCR or LAR)—described by Barany, *Proc. Natl. Acad. Sci.* 88:189 (1991). In LCR, four oligonucleotides, two adjacent oligonucleotides which uniquely hybridize to one strand of target DNA, and a complementary set of adjacent oligonucleotides, which hybridize to the opposite strand are mixed and DNA ligase is added to the mixture. Provided that there is complete complementarity at the junction ligate will covalently link each set of hybridized molecules. Importantly, in LCR, two probes are ligated together only when they base pair with sequences in the target sample without gaps or mismatches. Repeated cycles of denaturation, hybridization, and ligation amplify a short segment of DNA. Because the four oligonucleotides used in this assay can pair to form two short ligatable fragments, there is the potential for the generation of a target-independent background signal. Another limitation is that the method can only be used for the detection of known genetic variations.

Self-Sustained Synthetic Reaction (3SR/NASBA)—described by Guatelli et al., *Proc. Natl. Acad. Sci.* 87:1874–1878 (1990) is a transcription-based nucleic acid amplification method that can exponentially amplify 200–300 base pair long RNA sequences at a uniform temperature.

With amplified target nucleic acid, several methods can be used for subsequent mutation and polymorphism detection and characterization. Such methods might be divided into two groups:

biological or specific, for example, RFLP, hybridization, Allele Specific Amplification (ASO) PCR, pyrosequencing, etc.

physical-chemical scanning methods, for example, SSCP, Denaturing Gradient Gel Electrophoresis (DGGE),Denaturing High Performance Liquid Chromatography DHPLC, cleavage based methods, etc.

Comprehensive reviews of techniques used for SNP/mutation detection are described in *Electrophoresis* No. 6/99, vol. 20 and U.S. Pat. No. 5,719,028.

Biological or specific methods are based on the recognition of a specific nucleic acid sequence, therefore they are primarily suitable for the detection of a known SNP/mutation. In contrast, the physical or scanning methods require no prior knowledge of investigated sequences and are used for detecting and/or identifying any SNP/point mutations. Thus, these methods can be used for such applications as screening of highly variable genetic regions.

An example of a biological method for detecting genetic diversity is competitive PCR, described in U.S. Pat. No. 5,582,989. In that method, two different sets of primer pairs are used to amplify a target nucleic acid sequence. According to this method, one set of primers recognizes the wild type sequence and the other set recognizes sequence containing the selected point mutation. Another example is a method used for detecting the specific SNPs presence in the target nucleic acid based on the Allele Specific Amplification (ASO) as described by Shuber (1997) in U.S. Pat. No. 5,633,134. Unfortunately, PCR reactions may generate false results due to amplification of nucleic acid sequences to which the primers are not perfectly complementary. Accordingly, depending on the reaction conditions (temperature, ionic strength) either set of competitive primers can prime elongation of either the wild type or the mutant sequence.

Another group of techniques developed for SNP/mutation detection and analysis is based on the hybridization properties of the NA (biochips), see, e.g., Sapolsky et al. (1999), U.S. Pat. No. 5,858,659; Nerenberger, M., et al. (2000), WO 0061805; Arnold, L., et al. (2000), WO 0050869. Also, the RFLP method mentioned above can be used for detecting genetic variability in amplified nucleic acid fragments.

However, with any of the techniques described above the nature of the suspected genetic variability must be known prior to testing. Thus, those techniques are inapplicable when one needs to detect the presence of a mutation/polymorphism of an unknown character and position.

Only the physical-chemical methods are capable of detecting either known, or unknown mutations, and polymorphisms in any selected genome of interest.

One of these physical-chemical methods called Denaturing Gradient Gel Electrophoresis (DGGE), is based on changes in electrophoretic mobility of analyzed NA/NA hybrids when subject to denaturing conditions. In the DGGE method, genetic variants can be distinguished based on the differences in melting properties of NA homoduplexes versus heteroduplexes, sometimes due to differences in a single nucleotide which results in changes in electrophoretic mobility. To increase the number of mutations that can be recognized by DGGE, nucleic acid fragments amplified by PCR reaction are "clamped" at one end by a long stretch of G-C base pairs (30–80) to avoid complete dissociation of the strands while allowing for complete denaturation of the sequence of interest (Abrams et al., *Genomics* 7:463–475 (1990); Sheffield et al., *Proc. Natl, Acad. Sci.*, 86:232–236 (1989); and Lerman and Silverstein, *Meth. Enzymol.* 155: 482– 501 (1987)). To increase the SNP/mutation detection rate, a temperature gradient is introduced during the separation of amplified NA target (Wartell et al., *Nucl. Acids Res.* 18:2699–2701 (1990)).

Some limitations of the DGGE method arise from the fact that the denaturing conditions (temperature and urea concentration) depend on the analyzed sequence, so there is a need for optimization of the denaturing conditions for each target sequence. Reproducibility of the method depends on the accurate gradient gel preparation and precise gel temperature control. Extra expense is often incurred from having to synthesize a GC clamping tail for each sequence to be tested. Further, the time required to analyze each sample is often quite lengthy.

One of the most widely used physical-chemical methods for SNPs/mutation detection and identification is Single Strand Conformation Polymorphism (SSCP). With SSCP analysis, single base differences in single stranded NA fragments are recognized by differences in their mobility during separation under native conditions (Orita et al., *Genomics* 5:874–879 (1989)). In native conditions the single stranded NA fragments adopt a secondary structure according to their sequence and actual physical conditions. Since the electrophoretic mobility of a single stranded nucleic acid molecule depends on its net electric charge and three-dimensional (3-D) conformation, modification of any single nucleotide in the DNA fragment can result in a different 3-D conformation and thus influence the separation mobility. In some cases, single nucleotide modifications, however, result in different 3-D conformation only under particular physical-chemical conditions, of which the most important are ionic strength, pH and temperature. Based on variables such as temperature and ionic strength, the number and energetic stability of 2-D conformers of any single stranded nucleic acid molecule can be calculated using the nearest-neighbor thermodynamics algorithm which is known to those skilled in the art and is available on-line at http://bioinfo.math-.rpi.edu/~mfold/dna/. The presence of energetically stable 2-D conformers is predictive of the formation of stable 3-D spatial conformers.

Despite the simplicity of administering the SSCP method and relatively high sensitivity (above 90%), some limitations of the SSCP method have been reported. The most important limitation is the difficulty in obtaining consistent results. This is caused by the lack of a theoretical background from which predictions of the optimal separation conditions may be based (ionic strength, pH, temperature) for a particular NA fragment. The observed variability of SSCP results, according to many authors, results from the inconsistency of the separation conditions and on the mutation location within the analyzed NA fragment (Glavac and Dean, 1993, Hayashi and Yandell, 1993, Liu and Sommer, 1944). For example, to lower the temperature influence on the electrophoretic separation, low voltage power has been applied, however this has resulted in lengthy times of separation of up to 12–14 hours. Sensitivity of the SSCP method could be increased to close to 100% by applying at least two different separation conditions for the analysis of the same target nucleic acids. The separation conditions which are most influential on the separation mobility of single stranded nucleic acids are the type of porous support, the chemical composition of the separation buffer and temperature (Liu et al. in WO0020853). However, the time and cost of such an approach rise proportionally to the number of additional separations applied to analyze the same set of samples and would be quite difficult to use in routine diagnostics.

Genetic variability can also be determined based on a special mass-spectroscopy-analysis of the target NA by Monforte (1998) WO98/12355, Turano et al. (1998) WO98/114616 and Ross et al. (1997) *Anal Chem.* 15:4197–4202. This method requires quite expensive and specialized equipment, which is a major consideration and drawback.

In summary, there is a strong need for analytical tools and methods that would allow for reliable, time and cost-effective and close to 100% detection of genetic variability in nucleic acids. To become a useful diagnostic or technological tool, it should operate in full automatic mode with the capability of analyzing several samples at the same time. Such tools and methods would allow for more widespread diagnostic screening of humans with predispositions for various life treating diseases than is currently possible which could result in changing the health care paradigm from diagnosis and treatment to disease prevention.

BRIEF SUMMARY OF THE INVENTION

The present invention relates to a method for changing the separation mobility of single stranded nucleic acids under native conditions by changing the physical and/or chemical conditions of the separation. In one embodiment, the method for changing the separation mobility include at least one change of temperature during the separation under native conditions of single stranded nucleic acids. Changes of the separation mobility of single stranded nucleic acids are used for detecting known and unknown single base changes in nucleic acids for, among other uses, research and diagnostics purposes.

The present invention is based on the discovery that changes in temperature during the separation of single stranded nucleic acids under native conditions increase differentiation of analyzed molecules based on the differences in the separation mobility of analyzed single stranded nucleic acid molecules.

Where the separation mobility of single stranded nucleic acids during separation under native conditions is altered, it is not intended that the invention be limited by the means by which the separation mobility is altered. In one embodiment, the physical conditions are altered to induce alterations in the separation mobility of single stranded nucleic acids during separation under native conditions. In a specific embodiment, the physical condition that is altered is temperature. In another embodiment, the chemical composition of the separating medium is altered to induce alterations in the separation mobility of single stranded nucleic acids during separation under native conditions. In one embodiment, the pH of the separation medium is altered. In another embodiment, the ionic strength of the separation medium is altered. In any of these cases, the change of conditions may manifest itself in a change of secondary and/or tertiary conformation of the target single stranded nucleic acids, as is schematically presented in FIGS. 1A and 1B.

The present invention contemplates materials and methods that change the single stranded nucleic acid mobility during separation by manipulating physical and/or chemical conditions. In one embodiment, the physical condition to be manipulated is temperature. Temperature is contemplated as particularly useful as it can be changed quickly, precisely and in a repeated manner during the separation. Further, the influence of the temperature on the secondary and tertiary structure of single stranded nucleic acids is significant.

The present invention relates to methods for changing the separation mobility of single stranded nucleic acids in a sequence dependent manner. The change of the separation mobility is used to screen for known and unknown mutations, including single base changes in nucleic acids. In one embodiment, the present invention provides a method for detecting conformational changes in single stranded nucleic acids during their separation comprising (a) providing the nucleic acid; (b) transforming the nucleic acid into one or more single stranded nucleic acid spatial conformer(s); (c) separating the conformer(s) under native conditions; (d) changing one or more conditions of the separation at least one time during the separation wherein the conformer(s) is capable of undergoing a conformational change. In such an embodiment it is the change in one or more of the conditions that can impart a change in conformation of the conformer; (e) detecting the mobility pattern of the conformers; by detecting the changes of secondary and tertiary structure, the method of the present invention can be used to identify and characterize variations in nucleic acid sequences. In one embodiment, the method further comprises step (f) comparing the mobility pattern of the conformer(s) with a mobility pattern of a control conformer(s). In such cases the sequence of the control single stranded nucleic acid may be related (e.g., a wild type control or a mutant sequence) to the nucleic acid of interest. In one embodiment, the target single stranded nucleic acid contains a fluorescent label and the detection of step e) comprises detecting said fluorescently-labeled fragments.

It is not intended that the invention be limited by either the nature of the separation medium used for nucleic acid separation nor the physical force used for nucleic acid movement through the medium. In one embodiment, the force used to move the nucleic acids through the medium is electric. In another embodiment, the force is based on pressure. In another embodiment, the nucleic acids movement through the medium is defined by capillary action.

The present invention contemplates different physical or chemical separation conditions (including, but not limited to, ionic strength, pH temperature, and viscosity), as well as the type and construction of the equipment used for separation of single stranded nucleic acid conformers under native conditions.

It is not intended that the invention be limited by the nature of the nucleic acid. In the above-described embodiments, the nucleic acid target may be comprised of single-stranded DNA, double-stranded DNA, or RNA.

BRIEF DESCRIPTION OF THE DRAWINGS/FIGURES

Figure 4A:
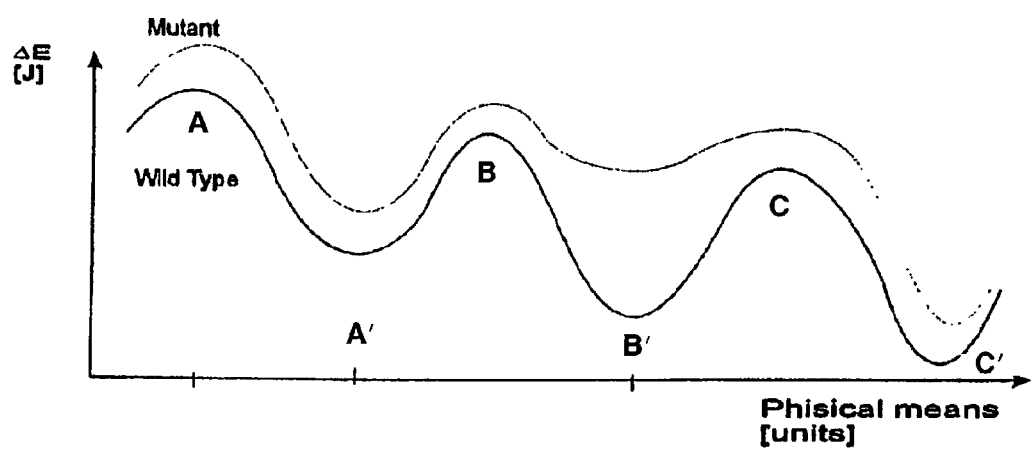
Figure 4B:
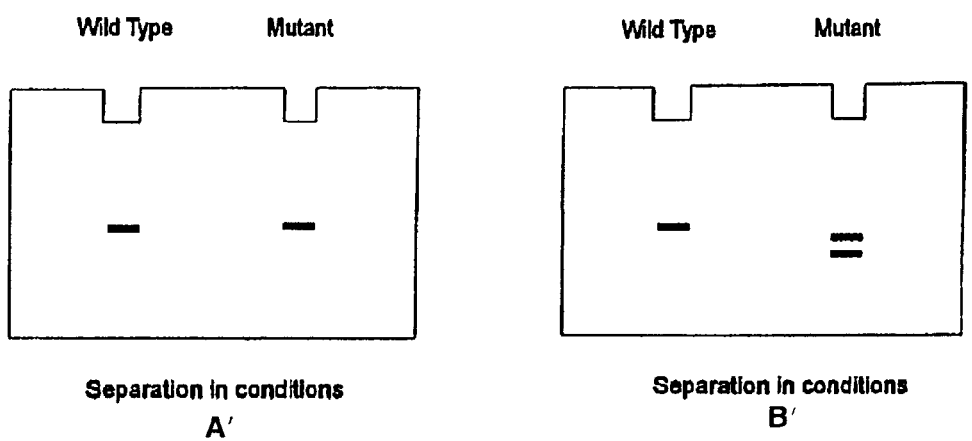
Figures 4C, 4D, 4E:
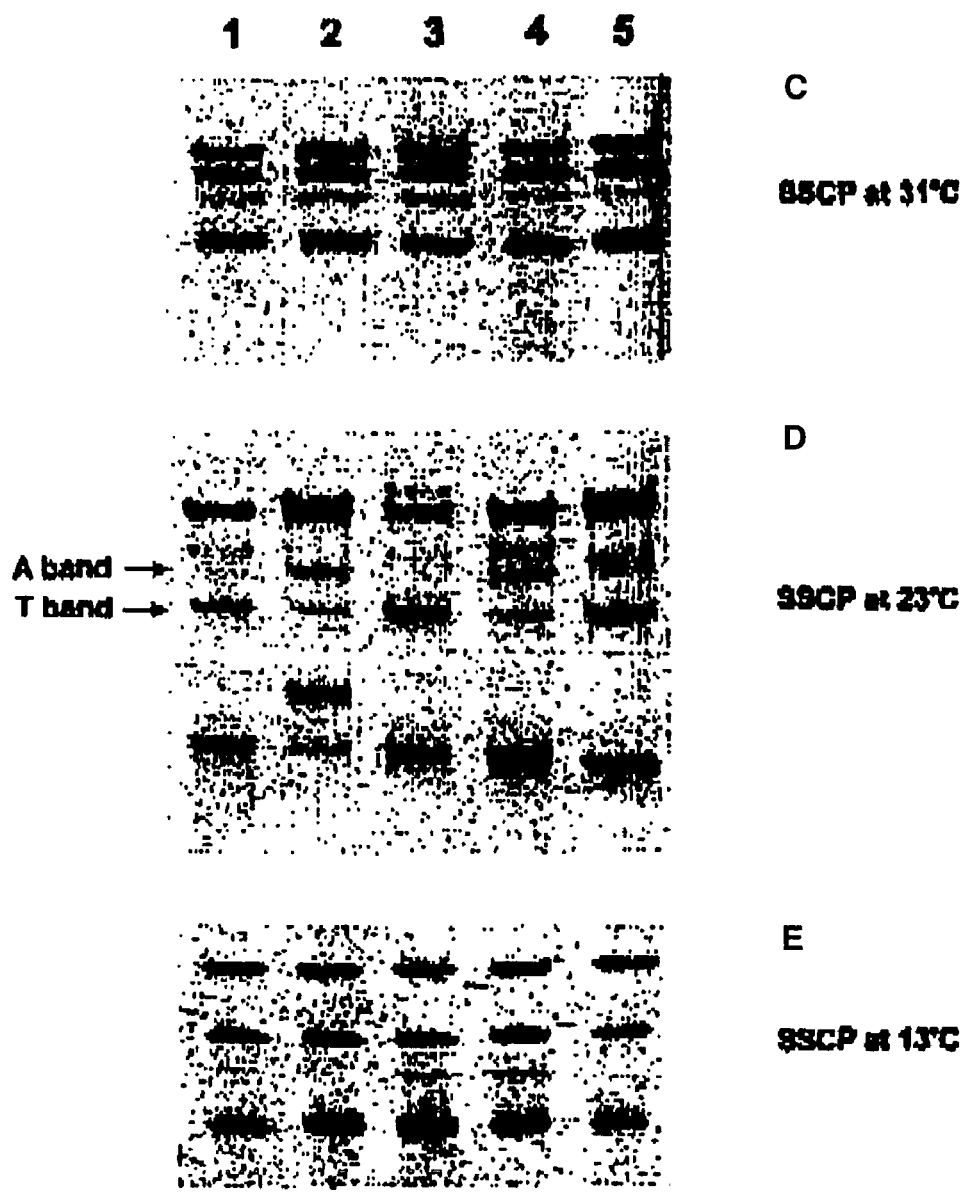

FIGS. 4A–4E describes the relationship between the physical means or conditions and the predicted stability of 3-D conformers and further demonstrates the influence of gel temperature on mutation detection by the SSCP method. FIGS. 4A–4B present a hypothetical example demonstrating that nucleic acids differing in a single base pair may exhibit the same or different single stranded 3-D conformers depending on the physical conditions. FIGS. 4C–4E present the results demonstrating the influence of gel temperature on mutation detection in exon 8 of the p53 gene by the SSCP method. Fragments of the genomic DNA isolated from blood were amplified by PCR. To perform SSCP, 10 µL of PCR product was added to 10 µL of denaturing buffer (0.1 M NaOH/10 mM EDTA) and incubated at 50° C. for 10 min. Prior to loading onto the gel 6 µL of ssDye buffer (0.1% bromophenol blue, 0.1% xylene cyanol FF in formamide) was added. The mixture was immediately loaded onto a 10% w/v native polyacrylamide gel with 10% glycerol. Electrophoresis was carried out in 0.5×TBE in the DNA Pointer Mutation Detection System at 10 W with gel temperatures set at 13° C., 23° C. or 31° C., separately. The separation patterns of ssDNA fragments were visualized by silver staining the gel. On all panels the same set of samples were analyzed. Lane 1, p53 wilde type; 2, GGA→AGA in codon 266; 3, TGT→TTT in codon 277; 4CGT→CAT in condon 273;5, CGT →TGT in codon 273. Gel temperature, (C) 31° C., (D) 23° C., (E) 13° C.

Figure 5:
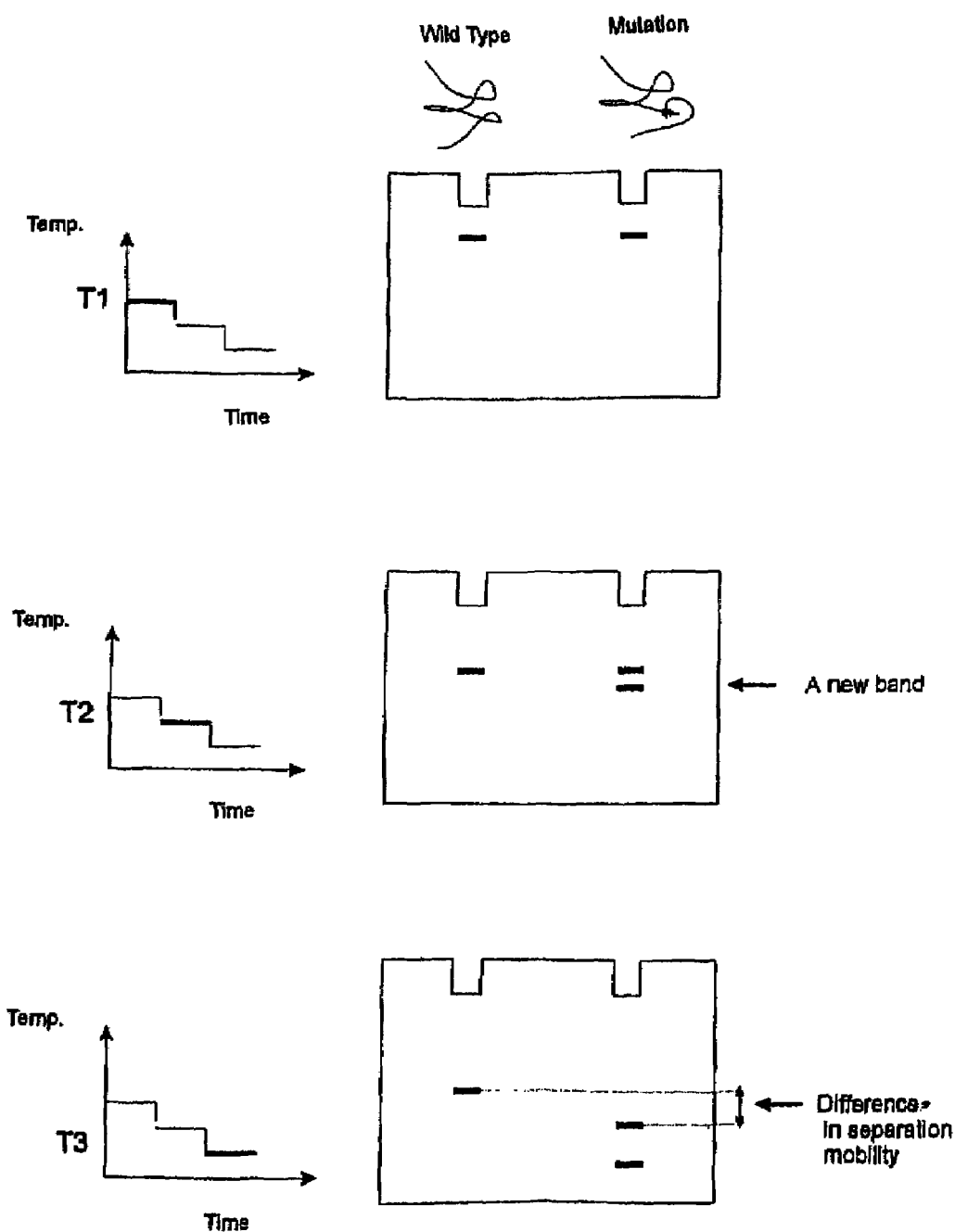

FIG. 5 provides a schematic of one embodiment of the detection method of the present invention, demonstrating the influence of changes in temperature on the electrophoretic mobility of two different single stranded nucleic acid conformers during separation under native conditions.

FIGS. 6A–6E illustrate a comparison of the SSCP and multitemperature SSCP (MSSCP) methods in analyzing the mobility pattern of single stranded conformers from exon 7 of the human PAH gene. Single stranded NA from seven different single point mutants from exon 7 of the human PAH gene are shown in lanes 1–6 and lane 8. The wild-type version is shown in lane 7. FIGS. 6A–6C depict the separation mobility pattern generated by the SSCP method at the indicated temperatures. FIG. 6D depicts the separation mobility pattern generated by the MSSCP method at the indicated temperatures. FIG. 6E shows the DNA sequence of silver stained bands eluted from the MSSCP gel.

Figure 7:
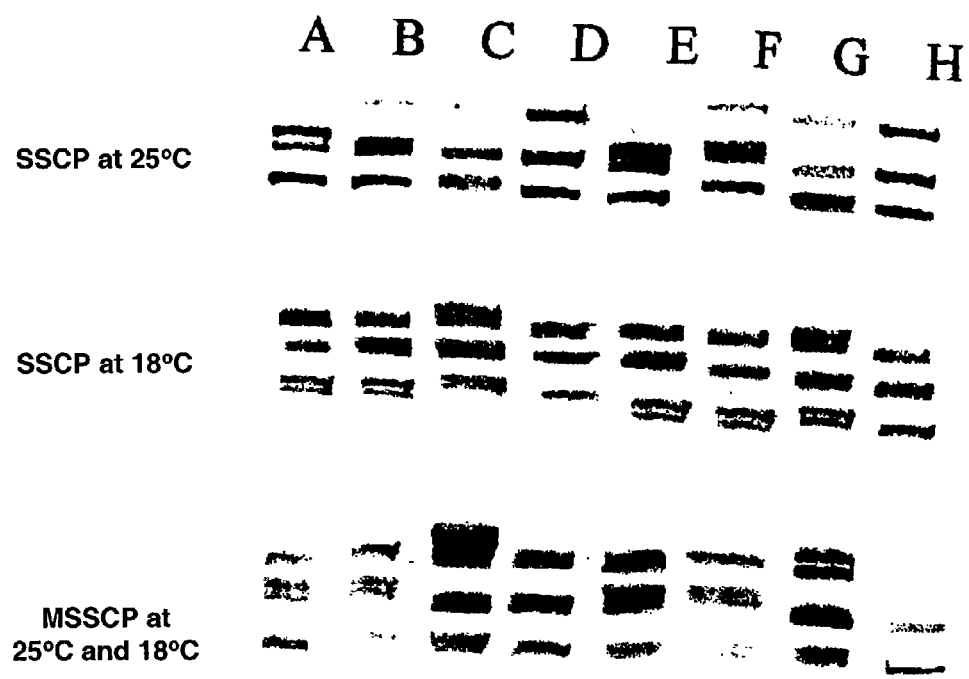

FIG. 7 presents a gel demonstrating human APOB-100 genotyping using the MSSCP technology.

Figure 8:
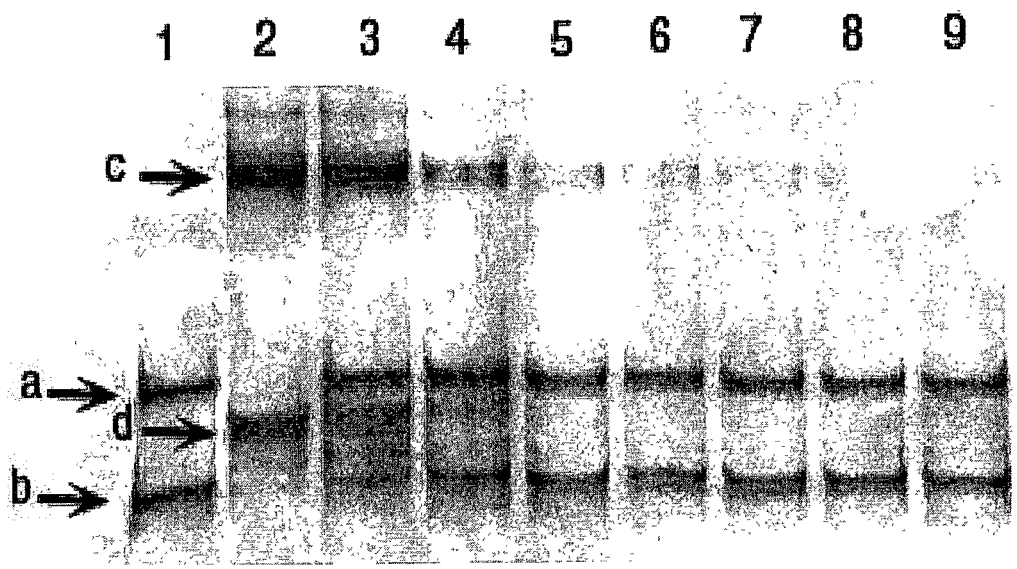

FIG. 8 presents a gel demonstrating detection of Hepatitus C virus variants in a heterogenous sample.

DETAILED DESCRIPTION OF THE INVENTION

The present invention provides materials and methods for efficient detection and/or characterization of nucleic acid sequences. In one embodiment, the methods of the subject invention involve changing the separation mobility of single stranded nucleic acids by changing the physical conditions during the separation of single stranded nucleic acids in native conditions. In a specific embodiment, the present invention relates to manipulating the temperature during the separation of the single stranded nucleic acids under native conditions. Changes in temperature during the separation of single stranded nucleic acids under native conditions increase the differentiation of the separation pattern and facilitate efficient detection of specific nucleic acid sequence variability.

To facilitate understanding of the invention, some of the terms used herein are defined below:

The (NA) nucleic acid that is to be analyzed can be any nucleic acid, e.g., genomic, plasmid, cosmid, yeast artificial chromosomes, artificial or man-made DNA, including unique DNA sequences, and also DNA that has been reverse transcribed from an RNA sample, such as cDNA. The sequence of RNA can be determined according to the invention preferably if it is capable of being made into a double stranded DNA form to be used as template DNA.

The abbreviation "ss NA" refers to single stranded nucleic acid.

The term "gene" refers to a DNA fragment that contains control and coding sequences necessary for the synthesis of a polypeptide, or its precursor.

The term "wild-type" refers to a gene sequence, common in nature, when it is the structural gene that is usually coding a functional protein.

The term "mutant" refers to a gene which displays an altered sequence when compared to a wild-type gene. The protein coded by a mutant gene could have altered characteristics when compared to the wild-type gene product.

The term "variation" as it relates to nucleic acid sequences, refers to a difference in nucleic acid sequence between two or more nucleic acids. Examples of sequence variation, include, but are not limited to, single base substitutions, point mutations, and single nucleotide polymorphism.

An individual may be "at risk" of developing a genetic disease or condition if that individual belongs to a group that exhibits a higher probability of disease or condition compared to the general population. Such a group may constitute only genetically related individuals, members of a particular racial group, members exposed to environmental stresses, etc. An individual may also be at risk if they display particular symptoms indicative of a particular disease or condition or progression thereof.

When referring to a conformer as "unique" compared to a control or to a population of nucleic acids it is intended to mean a conformer that exhibits a mobility or separation pattern that is not common to the control or all members of the population.

By "native conditions" it is meant conditions in which the ss NA adopts a distinct spatial conformation resulting from intramolecular interactions. Native conditions promote interactions between the side groups of the ss NA and depress free rotation about some or all bonds in the chain of the ss NA. Under native conditions, the ss NA does not have free rotation about all bonds in the chain, and does not lack all interaction of its side groups, as it does in a random coil. The conformer that results is amenable to changing its conformation by alterations of physical and/or chemical conditions. Usually the native conditions are defined by the most critical physical and/or chemical conditions which affect the spatial conformation, including but not limited to, temperature from 0.0°–50° C., ionic strength from 0.0–1.0 M KCl, and a pH from 6.0 and 9.0.

The term "native" can mean either the conformation of the ss NA as it exists in nature or a form of the ss NA that possesses secondary structure. "Denatured" means a form of the ss NA that has less secondary structure than that which is called native. Accordingly, the ss NA of the invention may be characterized, preferably electrophorsed, under conditions in which it possesses at least some secondary structure, and such conditions would still be considered to be "native conditions," even though such conditions do not allow for the full secondary structure that is found in nature. As long as the spatial conformation found under such "native conditions" is such that it allows for the manifestation of a less native (more denatured) structure, such conditions are useful as "native" conditions within the meaning of the invention. Accordingly, a ss NA can be "partially denatured" under native conditions as compared to the structure such ss NA assumes when not partially denatured, and such molecule and such conditions would still be useful in the method of the invention.

"3-D" and "2-D" are abbreviations of three-dimensional, two dimensional spatial conformation.

The term "conformer" refers to a particular 3-D or 2-D spatial conformation of a single stranded NA molecule. It is known that any single stranded NA molecule can adopt different 3-D conformations depending on the NA sequence and surrounding physical and/or chemical conditions. Stability and 2-D conformations of single stranded NA molecule may be estimated based on such models as the nearest-neighbor thermodynamics algorithm model (Santa-Lucia, Jr., *Proc. Natl. Acad. Sci. USA* 95:1460–1465 (February 1998)). That model demonstrates that for any single stranded NA molecule, several 2-D conformations might be achieved. The biggest influences on the 2-D conformation of a given single stranded NA molecule include temperature, ionic strength and pH. It can be also seen from the nearest-neighbor thermodynamics algorithm model that the optimal range of temperatures which should be used to induce 2-D conformation changes is: 0.0°–50° C. under native conditions.

The phrase "mobility pattern" refers to spatial or time distribution of single stranded NA conformer(s) as the result of their separation. Conformers are generated from any nucleic acid target without reference to a wild-type or other control. The invention contemplates the use of the subject method for both identification based on the "mobility pattern" of nucleic acids without reference to a control and identification of mutant forms of nucleic acid by comparison of the mutant form with a wild-type or known mutant control.

The term "oligonucleotide" refers to a molecule with at least two deoxyribonucleotides or ribonucleotides. In practice, the molecule has greater than ten deoxyribonucleotides or ribonucleotides. The exact size of the molecule will depend on many factors, which depends on the ultimate function or use of the oligonucleotide.

The term "primer" refers to an oligonucleotide which is capable of acting as a point of initiation of NA synthesis when placed under conditions in which primer extension is initiated.

The term "label" refers to any atom or molecule which can be used to provide a detectable signal, and which can be attached to a nucleic acid. Labels may provide signals detectable by any physical measure, including electromagnetics, fluorescence, radioactivity, X-ray diffraction or absorption, magnetism, and the like.

"Optimal separation conditions" refers to a set of conditions that yields the most distant separation of conformers present in a sample, with the most even signal intensity between the bands. Optimal separation conditions also refer to those conditions which generate distinct mobility patterns for a given set of nucleic acid molecules which differ at a single base locus. Examples of conditions, include, but are not limited to, temperature, ionic strength, and pH.

The term "template" refers to any nucleic acid molecule that can be used for amplification in the invention. RNA that is not naturally double stranded can be made into double stranded DNA so as to be used as template DNA. Any double stranded DNA or preparation containing multiple, different double stranded DNA molecules can be used as template DNA to amplify a locus or loci of interest contained in the template DNA.

Depending on the conditions and primary sequence, nucleic acids assume secondary structure. Nucleic acids with at least one single base difference can assume different 2-D and/or 3-D structures, which result in their difference in separation mobility. Recording the separation of said different nucleic acids in time or space, as schematically represented in FIG. 4, results in different separation patterns. Even a single base change can affect the separation mobility pattern of single stranded nucleic acids.

According to the method of the present invention, molecules used for separation are those which possess the 3-D structures formed after renaturation of complete denatured target nucleic acids. The 3-D structure will be governed, inter alia, by the tertiary structure of the ss NA. The tertiary structure will reflect many different forces, including hydrogen bonding, hydrophobic interactions, van der Waals forces, charged attraction (ionic bonds), and charge repulsion. Conditions that disrupt or induce any one or more of these forces can be used to alter the mobility pattern of the ss NA according to the method of the invention. Preferably, conditions that disrupt one or more of these forces are used in the method of the invention.

The denaturation of nucleic acids may be achieved by treating them with physical, chemical or enzymatic means which disrupt the secondary nucleic acid structure such as low (<3) or high pH (>10), high temperature, low salt concentrations or chemicals, like, e.g., urea, formamide or proteins (e.g., helicases) or a combination of these means. One embodiment of the present invention combines high temperature (about 100° C. in the presence of formamide or urea. In a specific embodiment, the nucleic acids are denatured in a solution containing about 3.0 M urea and 0.1 M NaOH. Lowering of the temperature, adding a salt, neutralizing the pH, withdrawing chemicals or proteins, all achieve folding or renaturation of the nucleic acid.

When denaturation means are removed, a collection of molecules with unique 3-D structures dependent on sequence and physical conditions is obtained. These conformers constitute a characteristic mark of the nucleic acid, which can be detected by separation of these conformers. This separation may be performed, for example on a porous media under optimized conditions.

Both changes in the sequence of a nucleic acid and physical conditions of the medium alter the spatial conformation of nucleic acids, which result in different separation patterns. The observations that the environmental conditions can so strongly influence the separation pattern increases the probability of obtaining different separation patterns when analyzing different nucleic acids having even very similar sequences.

In a preferred embodiment, the mobility pattern is altered due to disruption of the helical structure of the ss NA.

The present invention provides methods for differentiating single strand nucleic acid molecules with putatively different sequences. The invention is related to a method for detecting a variation in a nucleic acid molecule compared to a control nucleic acid molecule comprising:(a) providing the nucleic acid; (b) transforming the nucleic acid into one or more single stranded nucleic acid spatial conformer(s); (c) separating the conformer(s) under native conditions; (d) changing one or more conditions of the separation at least one time during the separation wherein the conformer(s) is capable of undergoing a conformational change. In such an embodiment it is the change in one or more of the conditions that can impart a change in conformation of the conformer; (e) detecting the mobility pattern of the conformer(s); By detecting the changes of secondary and tertiary structure, the method of the present invention can be used to identify and characterize variations in nucleic acid sequences. In one embodiment, the method further comprises step (f) comparing the mobility pattern of the conformers with a mobility pattern a of control conformer(s). In a further embodiment, the invention further comprises isolating the conformer(s) that is unique to the nucleic acid compared to the control nucleic acid conformer(s); and determining the nucleic acid sequence of the unique conformer. In a further embodiment, the isolation of the unique conformer is by electro-elution.

In accordance with the present invention, a change in the mobility pattern of the single stranded nucleic acid conformers can be obtained by solely applying changes to the physical or chemical conditions during the separation process. In a specific embodiment, the physical condition that is changed during the separation process is the temperature. In another embodiment, a change in the mobility pattern can be obtained by applying temperature changes in combination with changes of other physical conditions during the single stranded nucleic acid separation. In another embodiment, changes in the separation mobility of single stranded nucleic acids may be achieved during separation by applying temperature changes in combination with chemical changes. Such chemical changes include, but are not limited to, changes in pH of the separation medium, changes in the ionic strength of the running buffer, or changes in the chemical composition of the buffer. In another embodiment, one or more than one physical condition is altered in combination with one or more than one chemical condition during the course of single stranded nucleic acid separation. One of ordinary skill in the art would also appreciate that physical conditions and chemical conditions may be altered simultaneously to achieve a higher probability of separation of single stranded conformers, or they may be altered independently of one another. It is also appreciated that there may exist as yet undiscovered physical and/or chemical conditions which may influence the separation mobility of the single stranded conformers and alteration of these conditions during separation under native conditions is encompassed by the present invention.

In one embodiment, nucleic acid separation may be performed by electrophoresis. The invention encompasses various types of electrophoresis procedures, including but not limited to polyacrylamide gel electrophoresis (PAGE), agarose gel electrophoresis, capillary electrophoresis, pulsed field electrophoresis, etc. Additionally, electrophoresis may be performed in various gel running buffers including, but not limited to Tris-borate (TBE), Tris-acetate (TAE), Tris-phosphate (TPE), alkaline, or Tris-glycine buffer.

Nucleic acid separation may also be performed by other methods known in the art, such as high performance liquid chromatography, or variations thereof, such as reverse-phase ion-pair high performance liquid chromatography (RP-IP HPLC). Separations may also be performed by denaturing high pressure liquid chromatography (DHPLC), thin-layer chromatography (TLC), or other chromatographic methods.

The sample nucleic acid can be obtained from any source including a bacterium, virus, fungus, protozoan, plant, animal or human. In one embodiment, the nucleic is obtained from a human source. In another embodiment, the nucleic acid is obtained from a cell, hair, tissue, blood, urine, semen, saliva, plasma, serum, amniotic fluid or mucosa.

The nucleic acid can be provided using any suitable method known in the art including but not limited to PCR (polymerase chain reaction), 3SR (self-sustained sequence reaction), LCR (ligase chain reaction), RACE-PCR (rapid amplification of cDNA ends), SDA (strand displacement amplification), SOE-PCR (splice overlap extension PCR), RT-PCR (reverse transcription-polymerase chain reaction) and direct cloning of the nucleic acid.

The amplified region of nucleic acid may be of any size suitable to allow detection of the single stranded conformers. In a specific embodiment, the nucleic acid fragments are from 200–400 nucleotides in length. In another embodiment, the nucleic acid fragments are digested with a restriction endonuclease to generate fragment sizes which may be analyzed prior to the generation of single stranded conformers and separation. In a specific embodiment, the size of the digested nucleic acid is less than about 400 nucleotide in length.

The instant invention may be applied to any nucleic acid separating equipment or any other sequencing environment involving nucleotide sequence variation determination or detection.

Changes of the separation mobility of single stranded nucleic acids can be utilized according to the subject invention for detecting known and unknown single base changes in nucleic acids for, among other uses, research and diagnostics purposes. For example, the method of the present invention may be useful in analyses at a known or unknown genetic locus or loci in an individual that may be at risk of developing certain genetic diseases or conditions. In another embodiment, multiple individuals or populations may be analyzed simultaneously in reference to a single genetic locus, or multiple known loci. It will be appreciated by those skilled in the art that such large-scale population analyses form the basis for establishing correlations between genetic variation and various phenotypes, such as a susceptibility to various diseases/conditions.

The nucleic acid that is to be analyzed can be any nucleic acid, for example, single or double stranded DNA, RNA, cDNA, or oligonucleotides.

In another embodiment, the genetic region of interest is suspected of harboring a single nucleotide polymorphism or mutation. The method can be used to determine genetic variation at multiple regions concurrently. In this embodiment, genetic loci are selected for analysis and the respective nucleic acids are transformed into single stranded conformers. The conformers are then separated concurrently under native conditions, for example in separate lanes of an electrophoresis gel, wherein the conditions of the separation are changed one or more times such that the conformers are capable of undergoing conformational changes, followed by detection of the various conformers. The conformers may then be compared to reference or control conformers for rapid genotype analysis.

In one embodiment, the regions of interest are amplified in separate reactions and ss DNA is separated, for example by electrophoresis, in separate lanes. In another embodiment, regions of interest are amplified separately and pooled prior to ss DNA separation. In a further embodiment, the regions of interest are amplified in a single reaction.

In another embodiment, the invention provides methods for identifying previously unknown variations in a genome. In this embodiment, nucleic acids are provided from more than one individual, and a region of the genome is selected for analysis. Any region of the genome may be selected for analysis. In one embodiment, the region is a coding region or a regulatory region. In another embodiment, the region of interest has been linked, or is suspected of being linked to a phenotype, such as a genetic disease or condition. The region of interest may be provided by amplification by PCR, direct cloning, or other known methods of isolation. Following isolation of the region of interest, single standed nucleic acid conformers are generated from each sample and subjected to separation under native conditions, wherein during separation, one or more conditions are changed at least once. In a further embodiment the condition to be changed is a physical condition. In a specific embodiment, physical condition to be changed is the temperature. Following separation, the single stranded conformers are detected and are compared with each other for differences in their mobility pattern. Differences in the mobility pattern of the conformers amongst various samples indicates genetic variation and uniqueness in that region of the genome. In a specific embodiment, the genetic variation is due to the presence of a SNP. In another embodiment, the genetic variation is due to the presence of an autosomal mutation. In another embodiment, the individuals who are screened are members of a family or group who are at risk of developing a genetic disease. In another embodiment the mobility pattern of ss DNA from non-afflicted individuals is compared with the ss DNA mobility pattern from afflicted individuals.

According to the method of the present invention, native conditions during the separation of nucleic acid conformers are changed at least one time. The conditions may be physical or chemical in nature. A change in the physical or chemical conditions increases the probability of obtaining new 2-D and/or 3-D structures during the analysis and increases the probability of obtaining different separation patterns.

According to the present invention, changing the medium temperature at least one time during separation increases the probability of obtaining different spatial conformations in analyzed nucleic acids. Thus, changes in temperature during separation can be conveniently and expeditiously used to detect single base changes in nucleic acid molecules. This embodiment of the method of the present invention is termed "Multitemperature Single Stand Conformation Polymorphism," (hereinafter the "MSSCP" process).

It is not intended that the invention be limited to changing the physical conditions to modify the analysis condition during separation under native conditions of ss nucleic acids in order to change the separation mobility. The present invention also contemplates changes to temperature, ionic strength, pH, and includes the addition of chemical additives such as glycerol. In a specific embodiment, with temperature as the measure of the system's thermodynamic energy, temperature is the condition to be changed.

The temperature condition may be changed once or more than one time. In one embodiment, the temperature is changed one time during separation. In another embodiment, the temperature is changed twice during separation of the nucleic acids. In another embodiment, the temperature is changed three times during separation of the nucleic acids. In another embodiment, the temperature is changed four times during separation of the nucleic acids. The temperature may also be changed 5, 7, 8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 times. The temperature may also be changed greater than 100 times during separation of the nucleic acids. The temperature may be either increased sequentially or decreased sequentially, or it may be changed in any direction. The temperature may also be changed in any increment, for example in 0.1, 0.2, 0.3, 0.4, 0.5, 0.6, 0.7, 0.8, or 0.9° C. increments, or it may be changed in larger increments such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65 degree increments. In one embodiment, the separation temperature can range from about 0.0°–65° C. In another embodiment, the separation temperature can range from about 0.1° C. to about 100° C.

In another embodiment, the mean pH of the separation medium may be altered during the separation of the ss NA conformers under native conditions. In one embodiment, the pH is changed one time during separation. In another embodiment, the pH is changed twice during separation of the nucleic acids. In another embodiment, the pH is changed three times during separation of the nucleic acids. In another embodiment, the pH is changed four times during separation of the nucleic acids. The pH may also be changed 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 times. The pH may also be changed greater than 100 times during separation of the nucleic acids. The pH may be either increased or decreased. The pH may be increased or decreased in 0.1 pH unit increments during separation. In another embodiment, the pH is either increased or decreased in 0.5 pH units increments. The pH may also be increased or decreased in any increment including 0.1, 0.2, 0.3, 0.4, 0.5, 0.6, 0.7, 0.8, or 0.9 pH unit increments. The pH may also be increased or decreased in larger increments, such as 1.0, 2.0, 3.0, 4.0, 5.0, 6.0, 7.0, 8.0, 9.0, and 10.0 pH unit increments. The pH may also be changed in larger than 10.0 pH unit increments. In another embodiment, the pH may be altered by both raising and lowering the pH at various times during separation for any desired number of times for any desired sequece. For example, the pH may increase in two steps and then decrease in 1 step, followed by an increase in three steps.

Target nucleic acids that may be analyzed by the subject MSSCP method include both RNA and DNA. Such nucleic acid targeting may be obtained using standard molecular biological techniques. For example, target NA may be provided from a tissue sample or from a culture, cells, bacteria, or viruses, and may be transcribed in vitro from a DNA template, or may be chemically synthesized. Furthermore, substrates may be provided from an organism, either as genomic material or as a plasmid or extra chromosomal DNA, or it may be a fragment of such material generated by treatment with a restriction endonuclease or other cleavage agents, or it may be synthetic.

Target nucleic acids may also be produced by amplification using PCR. When the target is a single-stranded molecule, the target may be produced using the PCR method with preferential amplification of one strand (asymmetric PCR).

Single stranded nucleic acids may also be conveniently generated in other ways. For example a double stranded molecule containing a biotin label at the end of one of the two strands may be bound to a solid support (e.g., a magnetic bead) linked to streptavidin moiety. The biotin-labeled strand is selectively captured by binding to the streptavidin-bead complex. A single-stranded target may also be generated in other ways known in the art, for example, by digesting one strand of a double-stranded molecule with an exonuclease.

Target nucleic acids may contain a label to aid in their detection following separation. The incorporation of a nucleotide can further comprise using a mixture of labeled and unlabeled nucleotide. The label may be a radioisotope (e.g., a $^{32}P$ or $^{35}S$-labeled nucleotide placed at either the 5' or 3' end of the nucleic acid or alternatively the label may be distributed throughout the nucleic acid (i.e., and internally labeled substrate). The label may be a nonisotopic detectable moiety such as a fluorophore which can be detected directly, or a reactive group which permits specific recognition by a secondary agent. For example, biotinylated nucleic acids may be detected by probing with a streptavidin molecule, which is coupled to an indicator (e.g., enzyme or a fluorophore).

One or both oligonucleotide primers used to amplify the nucleic acid may contain a tag at the 5' terminus. The tag can be used to separate the nucleic acid of interest from the template nucleic acids. Additionally, after amplification, purification, and denaturation of the nucleic acids, the tag can be used to separate and purify one strand of the nucleic acid from its complementary strand. Purification of single stranded nucleic acid prior to separation will prevent reannealing of the single stranded nucleic acid with its complementary strand as well as decrease the number of single stranded nucleic acids which will be analyzed. In one embodiment, either the sense or the antisense strand is purified from its complementary strand through the use of a tag. In a specific embodiment, the use of the tag minimizes the number of single stranded nucleic acids for analysis, especially when a conformer of a single stranded nucleic acid from the sense strand and a conformer of a nucleic acid from the antisense strand have a similar mobility. Removing either the sense or the antisense strand prior to separation may facilitate detection and genotype analysis.

In another embodiment, the unlabeled nucleic acid is visualized by staining with silver ions or available single strand nucleic acid commercial stains, such as SYBYR GOLD (Molecular Probes, Inc.) or GELSTAR (Biowittaker, Inc.). Also when sufficient quantities of DNA are available for the analysis, absorbance of nucleic acid fragments allows for parallel analysis of several samples. Such an approach is especially useful for automated comparisons of e.g. wild-type and mutant forms of a gene separated on the same gel.

The spatial conformers of a target nucleic acid with different 3-D conformations can be analyzed and resolved using several methods including electrophoresis, chromatography, and fluorescence polarization. The invention is illustrated using electrophoretic separation. However, it is noted that the separation of the target conformers is not limited to electrophoresis. Separation of single stranded nucleic acid conformers in an electric field is described to illustrate the method of the invention because electrophoresis is one of the most popular methods used for molecular separations.

The subject MSSCP reaction is useful in providing a rapid and cost effective screen for single base sequence differences between nucleic acid molecules. To optimize the MSSCP reaction for any desired nucleic acid target (e.g., a wild-type nucleic acid and one or more mutant forms of the wild-type nucleic acid), it is convenient to use the wild-type form and one single base pair mutant to determine the best MSSCP conditions (temperature steps and salt concentration) which allow the target molecules to form two distinct separation patterns.

To establish optimal conditions for analysis of a particular NA fragment, it is advised to perform the first separation in a desired selection of temperature increments, for example four. For example, the temperature may begin at 45° C., and proceed in a stepwise manner to 30° C., 15° C., and 5° C. Additionally, the temperatures at which the nucleic acids have stable 2-D conformers may be predicted using the nearest neighbor thermodynamics algorithm available at http://bioinfo.math.rpi.edu/~mfold/dna/. Separations may then be performed utilizing combinations of those temperatures at which stable 2-D conformers are predicted. One of ordinary skill in the art will also appreciate that further optimization may be required in order to establish the best temperature conditions for MSSCP analysis for a given nucleic acid. In another embodiment, the ionic strength of the separation buffer may be optimized. For example, this may be performed by running two MSSCP separations, each in separation buffer with a different salt concentration, ranging between 5 mM and 35 mM. It is not intended that the salt utilized limit the present invention. The salt utilized may be chosen from potassium chloride, sodium chloride, etc. Likewise, other factors affecting nucleic acid structures, such as, formamide, urea, or pH may be optimized for each separation.

The method of the subject invention results in a reproducible pattern of fragments. The total time of slab gel electrophoresis is typically about 55–90 minutes and considering that typically about 30 samples may be analyzed in parallel, the time required for separation and analysis works out to less than 3 minutes/sample. The short time of electrophoresis (3 min/sample), and close to 100% accuracy attributable to the precise medium temperature control for separation make this method of analysis very suitable for the rapid screening of genetic variability in genome-population-wide surveys.

The methods of the present invention may be used for applications such as cancer diagnostics, tissue typing, genetic identity, bacterial typing, mutant screening in genetic crosses, etc. One aspect of the MSSCP method is that the pattern of separated conformers under a particular combination of physical and/or conditions constitutes a characteristic fingerprint, so a potential mutant can be compared to previously characterized mutants without the need for direct sequencing. This aspect of the invention makes it an ideal platform for rapid and accurate genotype analysis. Also, conformers that have different mobility compared to the wild-type or control conformers can be isolated directly, e.g. by electro-elution from a gel slice, and subsequently sequenced without the need for cloning. This significantly improves the sequencing reaction quality since only one single stranded NA is used for the reamplification reaction. Thus, this approach can facilitate discovery of new SNP or single point mutations.

The ability to detect specific nucleotide alterations or mutations in NA sequences has a number of medical and non-medical utilities. For example, methods capable of identifying nucleotide alterations provide a means for screening and diagnosing many common diseases that are associated with SNPs. Methods that can quickly identify such changes or mutations are also valuable in taking prophylactic measures, assessing the propensity for disease, and in patient counseling and education. As for non-medical applications, such methods have value in the detection of microorganisms, resolving paternity disputes and in forensic analysis to identify perpetrators of crimes.

The methods of the invention may also be used in molecular archeological studies such as the study of ancient DNA. Such studies are useful, for instance in tracing evolutionary lineages, establishing migration patterns, or establishing evolutionary relationships between various specimens.

In another embodiment, methods of the present invention may be used in forensic applications. The target nucleic acid(s) can be obtained from non-living sources suspected of containing matter from living organisms. For example, in the instance of samples obtained for forensic analysis, the target nucleic acids can be obtained from samples of clothing, furniture, weapons and other items found at a crime scene. Methods of the invention can also be utilized in various identification applications, such as in the field of forensic medicine or paternal testing. In the case of forensic analysis, polymorphisms in specific genes can be determined in, for example, blood, semen, hair, or other biological material obtained from a crime scene to indicate whether a particular suspect was involved in the crime. In like manner, polymorphism analysis may be utilized in disputes to aid in determining whether a particular individual is the parent of a certain child. The ability to use the methods of the invention to make rapid genotyping determinations provides a powerful tool in genetic analysis and ascertaining the susceptibility of an individual to a disease. For example the methods of the invention could be useful in determining whether an individual may be homozygous or heterozygous for an allele associated with a particular disease. For example, if a particular allele is implicated in the etiology of disease, an individual that is homozygous for the allele may be at higher risk of having or developing the disease than a heterozygote or a homozygote for the other allele. The heterozygote, however, is a carrier of the allele associated with the disease. Such knowledge can be useful in prenatal and other types of medical and genetic counseling, for example.

With knowledge gained from the genotyping methods described herein clinicians can conduct prenatal testing using cells obtained from a fetus to check for a variety of inheritable diseases, such as those diseases associated which are associated with a SNP or mutation. The methods can also be used to identify carriers of mutant alleles. Such information can be of use by a couple prior to conception as they evaluate the risks of having a child with certain birth defects or inheritable diseases.

The methods can be used in a number of different applications. For example, in the medical field, the methods of the invention can be used to determine which allele is present at a single nucleotide polymorphic (SNP) site or to detect mutations at a particular site. Because many diseases are associated with SNPs or mutations, the methods can be used in a variety of diagnostic, research and prognostic applications. In addition, for diploid subjects, the methods can be used to determine if the individual is homozygous or heterozygous for a particular allele, i.e., to determine the genotype of the individual. This is an important capability because individuals that are homozygous for an allele associated with a disease are at greater risk than individuals that are heterozygous or homozygous for the allele that is not linked to the disease. Furthermore, individuals that are homozygous for an allele associated with a particular disease sometimes suffer the symptoms of the disease to a greater extent than heterozygotes.

In addition to causing or affecting disease states, point mutations can cause altered pathogenicity and resistance to therapeutics that target certain microorganisms. In another embodiment the invention provides methods for identifying nucleic acids belonging to distinct species, strains, quasi-species, or other variants within a sample of nucleic acids. The sample of nucleic acids may contain one or more than one distinct species, strain, quasi-species, or other variant that possesses highly related nucleic acid sequences. This embodiment is particularly useful in the analysis of a sample that has been infected or contaminated with a pathogen or microbe that undergoes rapid genetic change, such as a virus. Currently, there is a need in the art for methods that can efficiently detect a variety of quasi-species within viral populations. Viruses typically undergo mutation at a high frequency, which may be due in part to selective pressures, such as antiviral therapy or host-derived immune responses. In a host infected with a virus, this selective pressure may result in the propagation of quasi-species or variants of the virus. These quasi-species may display unique properties compared to the wild-type virus, such as resistance to a particular drug or treatment. In accordance with this, the methods provide for a fast and efficient way to screen for potential new drug targets. The nucleic acid encoding the potential new drug target may be easily detected by establishing that a particular variant is enriched following treatment. The variant may contain one or more than one mutations which render the mutant resistant to a particular drug or treatment. Establishing that particular genotypes may be either sensitive or resistant to particular treatments or drugs will ensure that the most effective treatments are prescribed. The method of the present invention provides for the detection and analysis of these nucleic acids in a sample. In a preferred embodiment, the nucleic acids of interest of the variants will differ from the wild-type nucleic acid at a single base pair locus. The nucleic acids may be provided from the sample by methods known in the art. In a preferred embodiment, the nucleic acids are provided by PCR. The method of the present invention provides a method for detecting conformational changes in single stranded nucleic acids during their separation comprising (a) providing a sample of nucleic acids; (b) transforming the nucleic acids into one or more single stranded nucleic acid spatial conformer(s); (c) separating the conformer(s) under native conditions; (d) changing one or more conditions of the separation of (c) at least one time during the separation wherein the conformer(s) is capable of undergoing a conformational change. In such an embodiment it is the change in one or more of the conditions that can impart a change in conformation of the conformer; (e) detecting the mobility pattern of the conformer(s). The method of the invention may further comprise (f) comparing the mobility pattern of the conformer(s) with a mobility pattern of control conformer(s). The method may further comprise isolating the conformer(s) and determining the sequence of the nucleic acid. In one embodiment, the method of isolation is by electroelution.

Additionally, the methods of the present invention may be used to quantify the relative amount of the variants in the sample. For example, it may be advantageous to determine the most prevalent genotype present in the sample so that an effective course of treatment may be prescribed. Establishing the relative amount of one particular quasi-species or variant in a population present in a sample further comprises the following: isolation of all of the nucleic acid conformers in a sample from the separation medium; reamplifcation of the nucleic acids in a quantitative manner using the isolated nucleic acid conformers as a template. Quantifying the relative amount of each conformer in the sample. In another embodiment, the reamplified nucleic acids may be sequenced and the relative amount of nucleic acid corresponding to a particular nucleic acid sequence is obtained. In another embodiment, the procedure may be used to isolate and reamplify some but not all of the nucleic acid conformers of a sample from the separation medium. In this embodiment, it maybe advantageous to isolate only the predominant conformers, or the less predominant conformers, or the conformers that are known to correspond to a particular sequence, or to a particular phenotype, such as drug-resistance. In this embodiment, the selected conformers are reamplified in a quantitative manner and the relative amount of the conformers is determined. In a further embodiment, the nucleic acids may be sequenced and the relative amount of the nucleic acids obtained.

In one embodiment the nucleic acid may be of viral, bacterial, fungal or protozoal origin. In another embodiment, nucleic acid of the may be of viral origin. Examples of viruses that may be analyzed by the method of the present invention include, but are not limited to human immunodeficiency viruses (HIV), hepatitus B viruses (HBV), hepatits C viruses (HCV), Epstein-Barr viruses, hanta viruses, Ebola viruses, influenza viruses, herpes viruses, vaccinia viruses, adenoviruses, flavi viruses, rhinoviruses, polio virus, small pox viruses, In another embodiment, the nucleic acid is of bacterial origin. The bacteria to be analyzed may be from grampositive or gram-negative organisms, or may be a typical. The bacteria may be aerobes or anaerobes. Examples of bacterial genera include but is not limited to *Streptococcus, Staphylococcus, Enterococcus, Corynebacterium, Listeria, Escherichia, Klebsiella, Serratia, Enterobacter, Proteus, Providencia, Citrobacter, Shigella, Salmonella, Haemophilus, Moraxella, Legionella, Neisseria, Pseudomonas, Clostridium, Peptococcus, Peptostreptococcus, Bacteriodes, Mycoplasma, Bacillus, Campylobacter* or *Chlamydiae*.

In another embodiment, the nucleic acid is of fungal origin. Examples of fungi include *Aspergillus, Mucormycosis*, and *Candida, Saccharomyces, Trichophyton, Malassezia, Exophiala, Piedraia, Trichosporom, Sporothrix, Wangiella, Fonsecaea, Pseudallescheria, Madurella*, In one embodiment, the nucleic acid is of is a protozoal origin. Examples of protozoans include, but are not limited to *Entamoeba histolytica, Giardia lamblia, Trypanosoma cruzi, Trypanosoma gambiense, Leishmania donovani, Plasmodium falciparum, Toxoplasma gondii* and *Pneumocystis carinii*.

The sample may be from any source, for example a bacterial, fungal, protozoal, plant, animal or human source. In another embodiment, the sample may be from an environmental or industrial source. Examples of environmental sources include, but are not limited to air, soil, tundra, water (lakes, streams, livers, oceans, hot springs, glaciers, and deep sea thermal vents). Industrial sources include but are not limited to waste streams, water sources, the fluid or solids inside a supply line, or a production lot. Industrial sources also include fermentation hosts or other culturing media, such as from a biological reactor or food fermentation process which include the production of dairy products (cheeses, yogurt, etc.) wine, beer, spirits, or brewing in general; or foodstuff, such as meat, game, fish, produce, or dairy products.

Additionally, the sample can be pre-treated prior to use, such as preparing plasma from blood, diluting viscous fluids, or the like; methods of treatment can involve filtration, distillation, concentration, inactivation of interfering compounds, and the addition of reagents. The sample may contain several different species, quasi-species or other variants with highly related nucleic acid sequences. For example, the quasi-species may be derived from the original infective pathogen or contaminating agent, and may arise through natural selection within the host or environmental or industrial sample.

The methods of the invention may also be used in agricultural applications, such as the genotyping of various plant varieties and screening for improved variants of the plants. Various animal husbandry and breeding applications may also be contemplated by the methods of the invention, including identification of improved producers of a particular animal product. Methods of the present invention may also be suitable for identification purposes of agricultural animals, or other animals, such as family pets.

The following examples serve to illustrate certain embodiments and aspects of the present invention and are not to be construed as limiting the scope thereof.

In the part which follows, the following abbreviations apply: amplicons (amplified fragments of DNA produced by the PCR reaction); vol (volume); w/v (weight to volume); v/v (volume to volume); DNA (deoxyribonucleic acid); ml (milliliters) M (molar); mM (milliMolar); EDTA (ethylene diamine tetra-acetic acid); SDS (sodium dodecyl sulfate); Tris (tris(hydroxymethyl)-aminomethane); TBE (Tris-Borate-EDTA, i.e,. Tris buffer titrated with boric acid and containing EDTA); PBS (phosphate buffered saline); PAGE (polyacrylamide gel electrophoresis); Perkin Elmer (Norwalk, Conn.); Promega Corp. (Madison, Wis.); Kucharczyk Inc. (Warszawa, Poland).

EXAMPLES

Example 1

Construction of the DNA Pointer System

Figure 1:
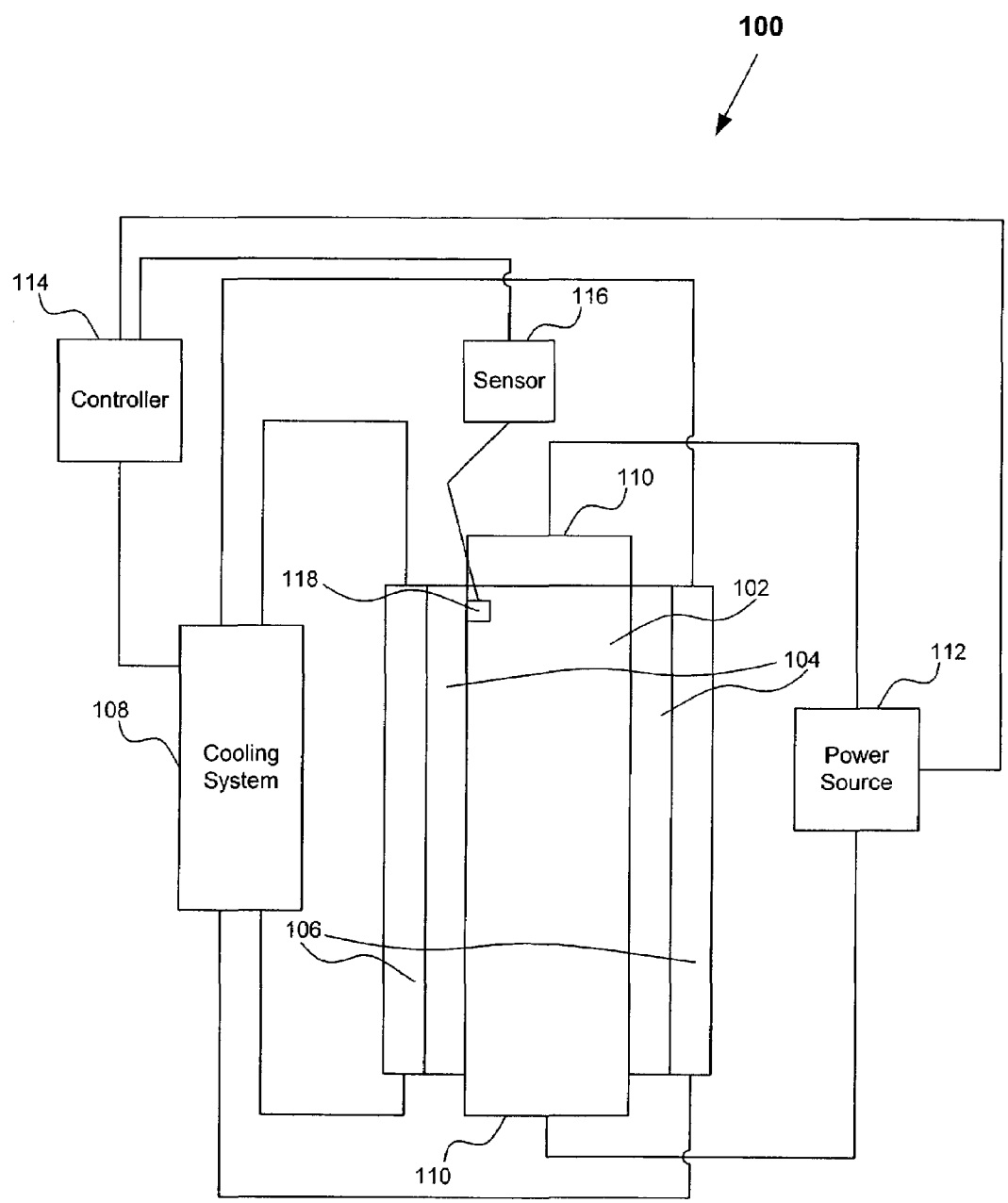
FIG. 1 is a block diagram showing an exemplary electrophoresis temperature control system having a planar gel holding device according to embodiments of the present invention.
Figure 2:
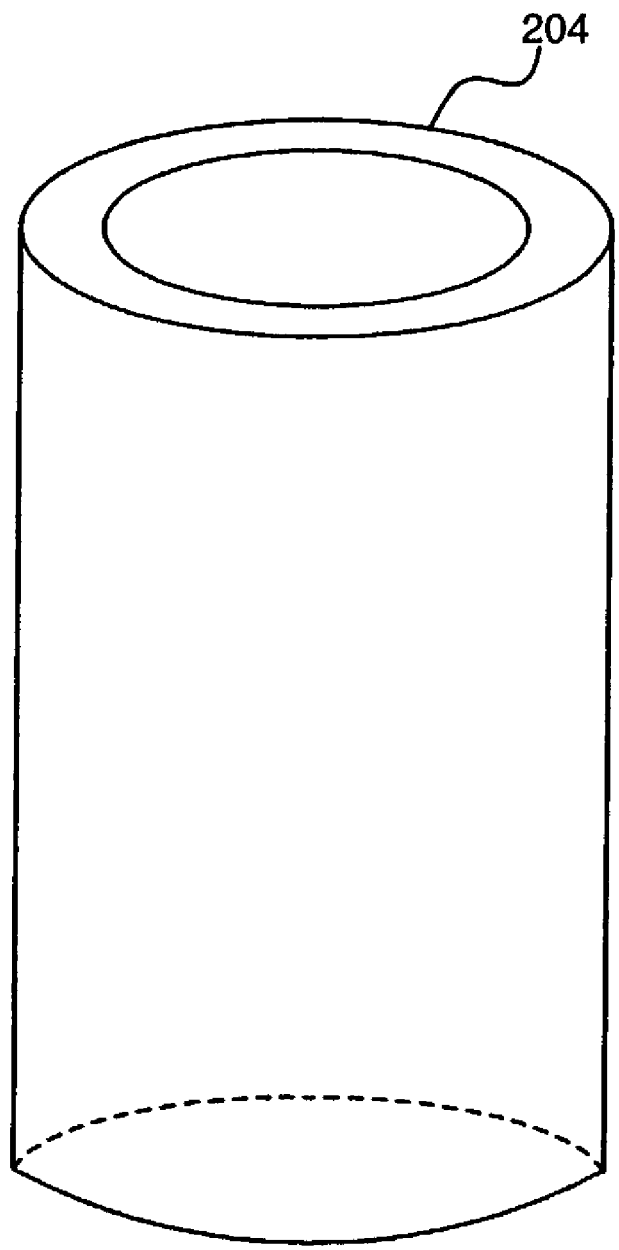
FIG. 2 is a perspective view of a cylindrical gel holding device according to an embodiment of the present invention.
Figure 3:
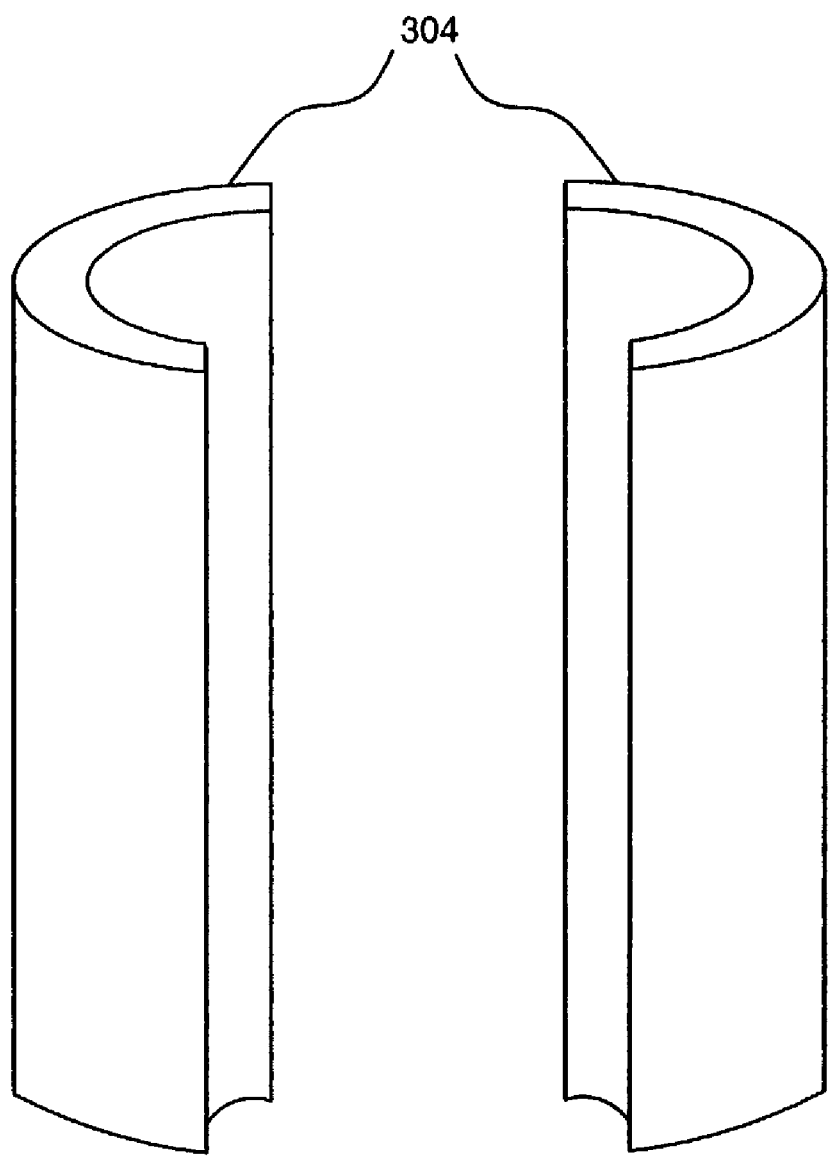
FIG. 3 is a perspective view of a semi-circular gel holding device according to an embodiment of the present invention.

FIG. 1 illustrates an electrophoresis temperature control system (e.g., a DNA Pointer System) 100 according to embodiments of the present invention. System 100 can be used to control temperature of a gel 102 during an electrophoresis process. Gel 102 can be held through use of holding structures (e.g., glass, plastic, or ceramic semi-circular supports, rods, any shaped plates, capillaries, etc.) 104. Although holding structure 104 is shown to be a planar plate in FIG. 1, as shown in FIGS. 2 and 3 a cylindrical structure 204 or a semi-circular structure 304, respectively, can also be used. Thus, the gel 102 can be held in any shape desired by an operator. A heat exchange module 106 is coupled to each holding structure 104. Heat exchange module 106 is also coupled to a cooling system 108. Cooling system 108 transmits and receives cooling medium (e.g., cooling fluids, or the like) that pass through heat exchange module 106. Holding structures 104 and gel 102 can be cooled through the flow of cooling medium. Input devices 110 (e.g., conductors, electrophoretic buffers, etc.) are coupled between ends of gel 102 and an electrical or pressure producing source 112, which causes an analyte to flow through gel 102. In embodiments using the introduction and flow of power through gel 102, a heat (Joule effect) proportional to the amount of current flow is generated inside gel 102.

A temperature profile of gel 102 during the electrophoresis process can be controlled by using a controller 114 coupled to a sensor 116. In some embodiments, sensor 116 can be a contact thermal sensor with a sensing portion 118 in contact with either gel 102 or any appropriate part of system 100. In other embodiments, sensor 116 can also be a non contact thermal sensor that detects heat radiating from gel 102. Heat is generated when the power flows through gel 102. Sensor 116 detects the heat and transmits signals based on the detection to controller 114. Through these signals, controller 114 monitors the generated heat. In various embodiments, controller 114 can be coupled to either cooling system 108 or source 112 to make sure gel 102 is maintained at a predetermined temperature for a predetermined amount of time, which is based on the heat detection. In this manner, the separation process, as described below, is maintained at a constant temperature during different stages. In some embodiments, system 100 can produce a gel temperature range of about 2°–65° C., gel temperature accuracy can be below about 1° C., and a gel size can be (W×H) 150×150 mm. One example for controlling the gel temperature with controller 114 can be based on using the following equation:

$$\Delta T = Qo/(2A) * (\frac{1}{4}(\Delta x1/\lambda1) + (\Delta x2/\lambda2) + (1/\lambda3))$$

Where:

ΔT—temperature different between heat exchange module 106 and gel 402

Qo—heat generated inside gel 102

A—surface of the heat conductivity (e.g. a gel holding structure 104) cooling surface Δx1—thickness of gel 102

λ1—thermal conductivity of gel 102

Δx2—thickness of holding structure 104

λ2—thermal conductivity of holding structure 104

λ3—convection heat transfer coefficient between holding structure 104 and heat exchange module 106

Example 2

The Influence of Gel Temperature on the Detection of Single Nucleotide differences by the SSCP Method FIG. 4 presents two hypothetical nucleic acid molecules which possess the same number of base pairs. The first is a wild type sequence which possesses three different local energetic minima under particular physical conditions, represented by A', B', and C' on the plot (FIG. 4A). The second sequence is a mutant sequence that differs in a single base pair compared to the wild-type sequence. The mutant sequence also possesses three different local energetic minima, represented by A', B' and C' on the plot (FIG. 4A). The energetic minima is related to a high probability of forming one or more stable 3-D conformers under those physical conditions. In contrast, the energetic maxima, represented by A, B, and C on the plot, is related to a low probability of forming one or more 3-D conformers (FIG. 4A). Due to the similarity in the energetic minima of the mutant and wild-type sequence, one could assume that under conditions A' and C' both molecules possess similar 3-D conformers. Under conditions represented by B', however, the wild-type sequence and the mutant sequence may be predicted to possess 3-D conformers that are unique and are different from each other, due to the difference in their local energetic minima.

Under optimal physical separation conditions B' from FIG. 4A, the differences in the separation mobility patterns between the wild type and the mutant nucleic acids are detected (FIG. 4B). For illustration purposes only, under conditions B', the mutant has two conformers which migrate more rapidly than the single wild-type conformer. Differences in the local energetic minima may be predictive of different mobility patterns and/or differences in the number of stable conformers between the nucleic acids of interest. In contrast, under physical conditions A' from FIG. 4A, the difference in the spatial conformation of the wild type and mutant nucleic acids does not influence the separation mobility to such an extent that measurement of the difference would be possible. Accordingly, no difference in the separation mobility pattern between the two analyzed single stranded nucleic acids was observed (FIG. 4B). This hypothetical example illustrates that separation of the wild-type and mutant single stranded nucleic acid molecules in native conditions may result in two different separation patterns if conditions for separation are optimal to resolve the spatial conformation difference. Where separation conditions are to remain constant throughout separation the most important influence on the separation profile is the separation medium temperature.

The conditions most often used during the SSCP analysis are: low power, room and cold-room temperatures. It was estimated using Eq. (1) that the actual gel temperature during SSCP electrophoresis performed without dynamic gel temperature control, may range from 13° C. (λ3=10 W/m²K) to over 31° C. when performed at cold-room or room temperature, respectively. To demonstrate the influence of the gel temperature on the detection of a single nucleotide difference by the SSCP method, a set of five alleles with single nucleotide differences in exon 8 of the p53 gene (Trzeciak, L., et al, *Nowotwory* 50:10–16 (2000)) were separated by means of SSCP under various gel temperatures in the DNA Pointer System.

Genomic DNA from tissue samples was isolated using proteinase K/phenol-chloroform extraction and resuspended in 10 mM Tris, pH 7.6. Exon 8 of the p53 gene was amplified from total genomic DNA using PCR. PCR reaction mixtures contained 100 ng of genomic DNA as a template, 0.2 mM dNTPs (MBI Fermentas, Vilnius, Lithuania), 1×PCR buffer (Perkin-Elmer, Norwalk, Conn., USA), 1 U Taq polymerase (Perkin-Elmer), 1.5 mM $MgCl_2$, 0.6 μM of oligonucleotides; sense; 5'-ATT TCC TTACTGCCTCTTGC-3' (SEQ ID NO: 1); antisense; 5'-AAG TGAATCTGAGGCATAAC-3' (SEQ ID NO:2). PCR in a final volume of 30 μl was performed in a PE 2400 apparatus and cycling conditions were as follows: 94° C. for 5 min. followed by 40 cycles at 94° C. for 10 sec., 52° C. for 31 sec., 72° C. for 30 sec. with the final extension at 72° C. for 5 min. When necessary, ss DNA bands were eluted from the SSCP gel and sequenced by DNA sequencing as described (Trzciak, L. et al., *Nowotwory* 50: 10–16 (2000)). DNA bands were eluted from the SSCP gel and sequenced by DNA sequencing as described (Trzciak, L. et al., *Nowotwory* 50: 10–16 (2000)).

PCR products (10 μL) were diluted in 10 μL of denaturing buffer (0.1 M NaOH/10 mM EDTA) and incubated at 50° C. for 10 min. Prior to loading on to the gel, 6 μL of ssDye buffer (0.1% bromophenol blue, 0.1% xylene cyanol in formamide) was added. The mixture was immediately loaded onto a 10% T, 2.5% C. w/v native polacrylamide gel, with 10% glycerol). Electrophoresis was carried out in 0.5×TBE (45 mM Tris, 45 mM boric acid, 1 mM EDTA, pH 8.0) in the DNA Pointer Mutation Detection System (Kucharczyk Co.), at 10 W at 13° C., 23° C., or 31° C. for 6 h. After electrophoresis, the gels were silver-stained using the Silver Stain kit (Kucharczyk Co.). After equilibration in 70% v/v methanol, the gels were dried in a Dry Out Slab Gel Drying Unit (Kucharczyk Col), scanned, and analyzed using Gelscan software (Kucharczyk Co.).

When the gel temperature was maintained at 31° C., all five samples exhibited identical electrophoretic patterns (FIG. 4C). Electrophoresis at a gel temperature of 13° C. produced an electrophoretic pattern different from the one observed for 31° C. (FIG. 4E). However, again no differences between the mutant and wild-type samples could be observed. When the gel temperature was adjusted to 23° C. and all other conditions of the analysis were kept unchanged, five different SSCP electrophoretic patterns, clearly differentiating all analyzed samples, were obtained (FIG. 4D).

Since all of the analyzed mutations in exon 8 of the p53 gene are located close to each other (See Brief Description of Drawings; FIG. 4) it was interesting to observe the stabilization and destabilization of a selected ssDNA conformer at 23° C., depending on the type of mutations. The ssDNA conformer, marked in FIG. 4D as "A band", was stabilized and at the same time the band marked as "T band" destabilized when the mutation changed the wild-type into A base (codon 273) (FIG. 4D, lanes 2 and 4). Similarly, destabilization of the band marked "A band" and stabilization of the band marked as "T band" occurred when the mutation changed the wild-type into T base (FIG. 4B lanes 1, 3, and 5).

These findings are consistent with the results obtained showing that 2-D structures generated using the nearest-neighbor thermodynamics algorithm (SantaLucia, Jr., *Proc. Natl. Acad. Sci., USA* 95:1460–1465 (Feb. 1998); available at http://bioinfo.math.rpi.edu/~mfold/dna/) show significantly different and energetically stable conformers when the temperature was changed by about 6° C. Taken together, these data support the idea that any ss DNA molecule could have an individual/optimal temperature for SSCP analysis. Optimal temperature ranges for a given ss DNA may be influenced by the G+C content of the nucleic acid (Kiyama, M., Fujita, T., *Biotechniques* 21:710–716 (1996). Nonetheless, changes in A+T base composition are also very easily detected by the SSCP method (Collins, A. et al, *Proc. Natl. Acad Sci. USA* 96:15173–15177 (1999)).

The influence of the gel temperature on mutation detection in exon 8 of the p53 gene, described above, suggests that SSCP false negative results may be due to inadequate gel temperature control rather than by a failure in method itself. Also suggested is that while comparing SSCP results from different laboratories, the simplified version of the heat transfer model from the gel to the outside must be applied (equation 1 from Example 1) to estimate the real gel temperature in each experiment. Such gel temperature adjustments should be considered, especially when performing the SSCP analysis in slab or capillary electrophoresis equipment with an air, solid heat exchange module or with long reaction time cooling systems.

Example 3

Detection of a Single Nucleotide Difference in the Exon 7 of Human PAH Gene; using MSSCP Analysis In order to evaluate the effect of the gel temperature changes during native electrophoresis on the electrophoretic mobility of ssDNA fragments, and compare the effectiveness of the MSSCP method over the standard SSCP approach, eight different sequenced SNPs from exon 7 of the human PAH gene were selected for analysis.

Amplification of Exon 7 Phenyloalanine Hydroxylase Human Gene

DNA preparation to amplify fragments from exon 7 of the human PAH gene was performed using standard procedures. Exon 7 was amplified by PCR reaction using primers AP287, 5'-TGCCTCTGACTCAGTGGTGAT-3' (SEQ ID NO:3) and AP423, 5'-CCCAAACCTCATTCTTGCAGCA-3' (SEQ ID NO:4). PCR reactions contained 100 ng of genomic DNA as a template, 50 mM Tris-HCl, 50 mM $MgCl_2$, MM of each primer, 0.2 mM of dNTPs, and 2U/100 µl of Taq polymerase (Kucharczyk Inc., Warsaw). PCR was performed in 25 µl cycling conditions were as follows: 94° C. for 5 min followed by 31 cycles at 94° C for 30 sec, 58° C. for 30 sec, 72° C. for 45 sec with the final extension at 72° C. for 5 minutes.

MSSCP and SSCP Analysis of Amplicons from Exon 7 of the Human PAH Gene

To generate single stranded DNA conformers, 1 µl of PCR product obtained as described above was added to 5 µl of 7 M urea, 2 µl of gel-loading buffer (0.25% (w/v) bromophenol blue, 0.25% (w/v) xylene cyanol FF, 30% (v/v) glycerol in water), and 4 µl of $H_2O$ to a total volume of 12 µl. The mixture was heated to 94° C. for 2 minutes and then cooled on ice. The cooled mixture was immediately loaded onto a 9% (w/v) native polyacrylamide gel (9% acrylamide:bisacrylamide-29:1 containing 5% (v/v) glycerol). Electrophoresis was carried out in 1×TBE in the DNA Pointer Mutation Detection System (Kucharczyk Inc., Warsaw) with 40 W of constant power at each temperature.

The first three separate SSCP separations were performed at the following constant gel temperatures: 34° C., 22° C., and 10° C. (for 1000 Vh). After electrophoresis the ss NA bands resolved in all gels were visualized by silver staining (Kucharczyk Inc., Warsaw, Silver Stain kit) followed by drying and scanning of the gel. The representative gels where separation was carried out at 34° C., 22° C., and 10° C. are shown in FIGS. 6A, 6B, and 6C, respectively.

At 34° C., the highest gel temperature, only four different electrophoretic patterns were observed (FIG. 6A). At gel temperatures of 22° C. and 10° C., six electrophoretic variants could be identified in each case (FIGS. 6B and 6C). In order to differentiate all eight samples based on their banding pattern, it was necessary to perform all three SSCP runs and combine the results. In all eight analyzed samples two classes of bands could be distinguished. The first class probably represents bands whose electrophoretic mobility significantly increases when the gel temperature is lowered and the second class whose electrophoretic mobility seems to be unaffected by the gel temperature (FIGS. 6A–6C).

The above observations prompted us to test the effect of changing the temperature during the SSCP electrophoresis on the mobility pattern of the conformers. The same set of known eight variants of exon 7 from the PAH gene was subjected to electrophoresis under the conditions specified above, except that for the first 333 Vh the gel temperature was kept at 34° C., then switched to 22° C. for the next 333 Vh and finally to 10° C. for an additional 333 Vh. Surprisingly, after this MSSCP electrophoresis, eight clearly different banding patterns were observed, which allowed differentiation of all analyzed samples after one single run (FIG. 6D).

All analyzed samples have clearly different electrophoretic patterns and are easily distinguished from each other and from the wild-type sample. The total time of the MSSCP electrophoresis was about 65 minutes (1000 Vh). After electrophoresis gels were silver stained for 30 minutes using Silver Stain Kit (Kucharczyk Inc., Warsaw). The gels were subsequently dried in the Dryout gel drying unit (Kucharczyk Inc., Warsaw) and then scanned and analyzed using Gelscan software (Kucharczyk Inc., Warsaw).

After silver staining the MSSCP gels the selected PAH conformer bands were cut off from the wet gels and DNA fragments from the slice were electro-eluted using the spin column format and subsequently sequenced. (BGM kit; Kucharczyk Co.). The eluted DNA fragments were reamplified by 35 cycles of PCR. Reamplified DNA fragments were purified and sequenced using the DNA sequencing Kit Big Dye Terminator Cycle Sequencing Ready Reaction (Applied Biosystems, US Foster City, Calif.). The PCR sequencing reaction was performed in a PE 2400 apparatus in a final volume of 20 µL and cycling conditions were as follows: 94° C. for 5 min followed by 25 cycles at 94° C., for 10 s, 50° C. for 5 s, and 60° C. for 4 min. The amplified DNA fragments were analyzed on the ABI Prism 310 Genetic Analyzer.

The sequences of all PAH samples were determined and compared to the sequences from the original fragments of genomic material isolated from blood. As presented in FIG. 6E, in all analyzed samples the DNA sequences were identical in both cases. The new technique was named MSSCP for Mutitemperature Single Strand Conformation Polymorphism.

The data gathered from these tests suggest that the above-selected temperatures can be sufficient conditions to detect all sequence variants in single stranded DNA fragments. Further, changing the gel temperature during electrophoresis increases the probability of detecting differences in the separation mobility of single stranded nucleic acids.

Other SNPs and point mutations in human genes have also been analyzed. These include APOE, APOB, and LHR and in each case a higher mutation detection rate or a clearer allele differentiation in comparison to the classical SSCP method was obtained. Thus, the sensitivity of the MSSCP method is significantly higher than the published SSCP mutation detection rate. Also, the total time of analysis is approximately 4 minutes, which includes separation by electrophoresis and silver staining. Additionally, the cost of chemicals ($0.20 per sample) are significant improvements over the classical SSCP method. Further, because of the low volume of PCR reaction with unlabeled primers, the cost of the PCR reaction, and so the overall cost of the SNP/mutation screening approach, was reduced. Combining the MSSCP analysis with a fast and effective electro-elution method of selected ss DNA molecules from the polyacrylamide gel for subsequent sequencing reactions forms a technical platform for an efficient, timely, and cost effective SNP and point mutation discovery system.

Example 4

Human APOB-100 Genotyping Using the MSSCP Technology

Familial defective apolipoprotein B-100 (FDB) is an autosomal dominantly inherited disease characterized by hypercholesterolemia and premature atherosclerosis. FDB has been identified based on DNA analysis in Caucasian populations of North America and in numerous European countries with a frequency ranging from 1:1250 to 1:500. Apolipoprotein APOB gene has been localized on human chromosome 2 (p23→ter). It comprises approximately 43,000 base pairs and contains 29 exons, and 28 introns. Apo B-100 protein is a product of the whole gene. The fragment rich in positively charged amino acids encoded by exon 26 is a potential Low Density Lipoprotein (LDL) receptor-binding domain. Apo B-100 is the only protein of LDL and it's binding to the LDL receptor is essential for the removal of LDL from plasma. The most common mutation in FDB is an adenine for guanine substitution (position 10,708) in complementary DNA of exon 26 of the APOB gene. It results in an arginine for glutamine change in the 3500 amino acid position of the protein. The mutation strongly reduces protein binding affinity to the LDL receptor. The occurrence of other mutations localized in the same 3500 site ($Arg_{3500}Trp$) or in its close proximity ($Arg_{3531}Cys$) were also reported.

Materials and Methods

Genomic DNA was isolated from the white blood cells by phenol/chloroform extractions and ethanol precipitation. A 320-bp fragment of 26 exon of APOB gene was amplified using the PCR method. For the MSSCP analysis the 5 µl aliquot of the PCR product was mixed with 60 of denaturing loading MSSCP buffer (5 µl of formamide and 1 µl of 0.25% bromophenol blue and xylenenecyanol in 50% glycerol), incubated in 95° C. for 5 minutes and cooled immediately on ice. DNA fragments were loaded onto 9% polyacrylamide gels (50:1) containing 5% glycerol in 1×TBE buffer. Gels were poured in Multipol DNA Pointer System (Kucharczyk, T. E.) with 1 mm spacers. Electrophoresis was carried out at constant voltage of 500 V at:

a) SSCP; 25° C.
b) SSCP; 18° C.
c) MSSCP; 25° C. and 18° C.

The total time of each analysis was equal. DNA fragments in the gel were visualized by staining with silver using Silver Stain Kit (Kucharczyk, T. E.)

Results and Discussion

The Multitemperature SSCP (MSSCP) method was used to distinguish three APOB gene point mutations in exon 26 from the wild type of APOB gene. First, four analysed alleles were identified by classic SSCP, using two different runs at 25° C. and 18° C. (FIG. 7). At 25° C. mutation $Arg_{3500}Gln$ could be distinguished from mutation $Thr_{3492}Ile$, but mutation $Arg_{3531}Cys$ could not be distinguished from the wild type. At 18° C., the mutation $Arg_{3531}Cys$ could be distinguished from the wild type, but mutation Arg3500Gln could not be distinguished from mutation $Thr_{3492}Ile$.

Next the MSSCP method was applied in one, four hour long run (25° C. for 1 hour and then 18° C. for 3 hours). Temperature changes allowed derection of all three mutations in one electrophoretic run. The precise gel temperature control by the DNA POINTER improves mutation detection. The application of the MSSCP technique significantly reduces the cost and time of APOB gene mutations analysis. This method because of speed, cost effectiveness and reliability could be useful in screening patients with hypercholesterolemia (especially with a family history for hypercholesterolemia or premature atherosclerosis) for FDB.

Example 5

Detection of the Heterogeneity of Samples Containing Genetic Material

RNA viruses like (Hepatitis C virus (HCV) and human immunodeficiency virus (HIV)) show a great genetic heterogeneity, due to incorporation of errors by the polymerase during replication. It allows them to survive in the changing environments, such as in a host, and select the viral population that is best suited to live in a particular environment. This mechanism of evolution leads to emerging virus species that are drug-resistant.

HCV isolates show four levels of genetic variability, types, subtypes, isolates and quasi-species, and are today classified into 6 types (1–6) and 80 sub-types (1a, 1b, etc. . . . ) (Simmonds P., et al. *Hepatology* 19:1321–1324 (1994)). The RNA sequence homology in the Core, E1 or NS5 regions is seen in at least 91% in isolates of the same genotype, 77–80% between the subtypes and 66–69% between the types of HCV. Quasi-species are genetically distinct variants of viruses. The distribution of different genotypes within the quasi-species plays an important role in terms of patient survival. The presence of multiple viral sequences and rapid apparition of new variants allows rapid selection of mutants best suited to the environment.

Current genotyping methods are limited in the terms of detecting minor variants of HCV. The hybridization techniques are not sensitive enough to detect minor viral variants. Direct sequencing is still the preferred technique but is also limited to detect minor variants of HCV to the level of 30% or 25%. An alternative approach is to clone PCR products and sequence clones. This method is very expensive time consuming and is unreliable in that the only minor variants of HCV will be identified only when a large number of clones are sequenced.

Here it is proposed a fast and cost-effective method for identification of HCV quasi-species and obtaining a homogenous template representing minor variants from a mixture of genetically distinct virus variants. The method PMES (PCR, MSSCP or SSCP, electroelution and sequencing) could be used to identify minor variants of a virus in HCV, HIV, or any other virus infection.

To demonstrate the capability of the PMES strategy for resolving the problem of genetic heterogeneity of staring material, two basic HCV NS5B genotypes 1a and 2c were analyzed by the PMES technology.

Materials and Methods

Amplification of the NS5B Region of HCV

Oligonucleotides:

The primers used for reverse transcription (RT) and the first round of PCR of the nucleotide sequence of NS5B region were as follows: (i) primers for RT and the first round of PCR: sense primer #243- 5'-TGGGGATCCCGTAT-GATACCCGCTGCTT TGA-3' (SEQ ID NO:5); antisense primer #242 -5'-GCGGAATTCCTGGTCATAGC CTC-CGTGAA-3' (SEQ ID NO:6) (ii) primers for second round PCR: sense primer #122 5'- CTCAACCGTCACT-GAGAGAGACAT-3' (SEQ ID NO:7); antisense primer #123 5'- GCTCTCAGGTTCCGCTCGTCCTCC-3' (SEQ ID NO:8).

RT-PCR Amplification

The nucleic acids were extracted from 100 µl of serum of an infected patient by the guanidinium thiocyanate-phenol-chloroform extraction method with minor modifications using the Total RNA Prep Plus isolation kit from A&A Biotechnology (Gdańsk, Poland) according to the manufacturer instruction. The RNA was reverse transcribed using MMLV reverse transcriptase (Invitrogen, Carlsbad, USA) in 42° C. for 60 min followed by 5 min in 95° C., in a reaction volume of 25 µl containing 10 pmol of the primers 243 and 242. The cDNA was amplified by PCR with 40 cycles using the primers mentioned above (94° C. for 30 sec, 50° C. for 45 sec, 72° C. for 1 min) and 1U of Taq polymerase (Invitrogen, Carlsbad, USA) according to the manufacturer's recommendations. 1 µl of PCR was subjected to another 20 cycles using primers 122 and 123 (94° C. for 30 sec, 50° C. for 45 sec, 72° C. for 45 sec) and 1 U of Taq polymerase (Kucharczyk T. E., Warszawa, Poland). Proof of specificity was obtained by running negative controls together with the patient's samples and by sequencing the amplified DNA.

The PCR Products Analysis by SSCP/MSSCP Method

For SSCP analysis PCR products amplified with primers 122 and 123 of two different HCV genotypes (1a and 2c) were analyzed. To evaluate the minimum co-infection detection level PCR products of genotype (1a and 2c) amplified with primers 122 and 123 were mixed in proportions ranging from 1:1 to 99:1. Next 2 µl of mixed PCR products were added to 6 µl of denaturing solution (100 mM NaOH, 10 mM EDTA), heated for 10 min in 55° C. and quickly cooled in ice-water bath. After that 2 µl of dye was added (0,02% bromophenol blue, 0,02% Xylene Cyanole, 30% glycerol). Samples were immediately loaded onto 9% native polyacrylamide gel (acrylamide: bis 29:1, in 0,75×TBE buffer) in the DNA Pointer System, (Kucharczyk T. E., Warszawa, Poland) and subjected to electrophoresis in 30° C. (100 V for 20 min, next 40 W for 70 min) in 0,5×TBE buffer. The preload run was 100 vH at 30° C. with 40 W of power. For MSSCP analysis, electrophoresis was performed at 35° C. and 25° C. for 50% of Vh each.

Nucleic Acid Staining and Elution

To avoid denaturation of DNA in the gel during staining, after electrophoresis the gel was divided into 2 parts. One part was stained using the Silver Stain kit (Kucharczyk T. E., Warszawa, Poland). After staining the stained part of the gel was gently put on the non-stained part of the gel in the manner to ensure that the appropriate genotype mixes were under the visible bands. The bands and the unstained fragments of the gel below them were cut out. The DNA fragments were electroeluted from the not-stained part of the gel using the Blue Gene Mashine system (Kucharczyk T. E., Warszawa, Poland). Electroelution was carried out for 30 min under 100V in 0.75×TBE buffer.

Reamplification and Quantification of Eluted ssDNA Fragments.

Eluted ss DNA fragments were used as matrix for a PCR reamplification reaction with primers 122 and 123 for 30 cycles in the Lightcycler (Roche Diagnostics Corporation, Basel, Switzerland) (94° C.—5 sec., 50° C. 15 sec., 72° C. 30 sec). The reaction contains 3 µl of (out of 20) eluted DNA fragments, 10 pm of primers 122 and 123,0,25×SYBR Green (Molecular Probes, Eugene, USA), 1 U of Taq Polymerase (Kucharczyk T. E., Warszawa, Poland). For sequencing the re-amplification was performed without the SYBR Green.

Sequencing

PCR products were purified with DNA Clean-Up kit (A&A Biotechnology, Gdańsk, Poland). The eluted DNA was subjected to a cycle sequencing reaction using the "DYEnamic ET Terminator cycle sequencing kit" (Amersham Pharmacia, Uppsala, Sweden) and primers 122 and 123. Sequence analysis was performed on ABIPrism 377 DNA Sequencer (AppliedBiosystems, Foster City, USA).

Mixed in Proportions 1:1 to 99:1

The representative get were separation was carried out is shown in FIG. 8. In lane 1 the 1a HCV genotype is loaded and in Lane 2 the 2c HCV genotype is loaded. Lane from 3 to 9 contains the mixture of the two genotype in the following proportions: [1a:2c]:Lane 3—1:1; Lane 4—9:1, Lane 5—19:1; Lane 6—29:1; Lane 7—49:1; Lane 8—59:1; Lane 9—99:1.

As it can be observed, even a 1% (FIG. 8, lane 9) presence of the HCV genotype 2c in the analyzed samples could be detected with this approach. While by direct sequencing of the mixed sampes the presence of the 2c quasi-species was not detected when it's level was below 50%.

TABLE 1

| The amount of PCR products of NS5B region from HCV 1a and 2c used for sample preparation: [1a:2c] | 1:1 | 9:1 | 19:1 | 29:1 | 49:1 | 99:1 |
|---|---|---|---|---|---|---|
| PMES of band c | 2c | 2c | 2c | 2c | 2c | 2c |
| PMES of band a | Ia | Ia | Ia | Ia | Ia | Ia |
| Direct sequencing of mixed PCR products | 2c/Ia | Ia | Ia | Ia | Ia | 0 |

After electro elution and quantitative reamplification of the N.A. material isolated form bands representing particular HCV virus genotypes (marked with letter a and b for HCV genotype 1a on FIG. 8, and letter c for HCV genotype 2c) we have been able to estimated the preliminary accuracy in the virus quasi-species amount determination using the PMES technology on the level of +/−28% based on the Lightcyckler (Roche Biosciences) real-time amplification.

Table 2

Accuracy of the Determination of the Relative Amount of the Quasi-Species based on the PMES Strategy The % composition of the mixture of HCV 1a and 2c PCR products used in the starting mixture preparation is described in the first row. In the row two and three the % composition of the analyzed samples based on the PMES approach are shown. The amount of particular ssDNA fragments in each samples was calculated by two different methods based on the procedures in the real time PCR machine (LightCylcer, Roche Biosciences, Inc))

| Proportion of 1a:2c based on the PMES | Proportion of 1a:2c PCR products in analyzed samples [%] | | | | |
|---|---|---|---|---|---|
| Starting material composition | 50 | 10 | 5 | 2 | 1 |
| Second derivative maximum method | 70 | 11 | 17 | 5 | 3 |
| Difference [%] | 40 | 10 | 140 | 150 | 200 |
| Fit points method, Arithmetic Baseline adjustment | 60 | 15 | 6 | 2 | 1,5 |
| Difference [%] | 20 | 50 | 20 | 0 | 50 |

Average Difference of arithmetic baseline adjustment = 28%

Discussion

PMES demonstrated a higher level of minor virus variant identification in comparison to direct sequencing. The PMES technology is a fast and cost-effective method that allows detection and identification of virus quasi-species. Minor subpopulation of viruses can be detected using MSSCP methods down to the level of 1% in a complex mixture of genetically distinct variants. After electroelution and re-amplification, excised bands could be used as a homogenous matrix for a subsequent sequencing reaction. That approach allows for fast and cost effective identification of the minor virus species or quasi-species present in clinical material at the 1% level in comparison to the total viral load.

SSCP and MSSCP is a reliable methods for detecting point mutations in PCR products when performed in well controlled conditions. But they are time consuming could last several hours when performed with under low voltage conditions to avoid gel overheating (McKechnie V. M., McCruden E. A, *Journal of Virological Methods* 92:131–139 (2001); Peters T., et al., *Journal of Virological Methods* 64:95–102 (1994)). A high-voltage, electrophoresis under precisely controlled conditions with accurate heat control capacity allows for clear separation of single-stranded DNA bands in up to 90 minutes.

Typically HCV quasi-species differ at least with few point mutations. When analyzing HCV genomes at the conserved regions (NC5) in order to detect the classical HCV species which differ in only one point mutation, well controlled electrophoresis conditions and temperature steps should be applied. Under the conditions used in the present study SSCP analysis allowed for detection of quasi-species representing 1% of the viral population. Based on our results demonstrating that the MSSCP approach allows for greater reliability in the detection of single base pair differences than the SSCP method, the MSSCP method should provide even greater sensitivity and detection. The minor subpopulation detection level is limited by the silver-staining detection level which is estimated to be 5 pg DNA/band.

The elution of the nucleic acids was performed with an electrical field that allow to shorten the procedure to 1 hour.

Additionally we quantified the eluted samples in real-time PCR. The results were consistent and the error margin was 28% percent when the Fit points method and Arithmetic Baseline adjustment approach was used.

The presented strategy PMES (PCR, SSCP or MSSCP, electroelution, sequencing) is an easy, cost-effective and fast method for identification of quasi-species of HCV. The minimum quasi-species detection level is evaluated to be 1%. The total time needed to identify a quasi-species is evaluated to be 3.5 h (PCR and sequencing not included) as described in Table PMES could be used in the identification of circulating drug-resistant species, before they become the major strains within a viral population. This could help to identify the resistant quasi-species before they become the major quasi-species and to apply a better treatment regimine for the patients who harbor the drug-resistant strains. For example, the method may be used to screen for drug-resistant quasi-species of HIV, Hepatitis B virus, HCV). The role of HCV drug resistance testing will be important in the clinical management and prognosis of HCV infection, as specific hepatitis drugs targeting HCV RNA helicase, HCV proteases as well as the RNA polymerase, come to the market.

In summary, the PMES approach has a much higher detection rate of minor variants when compared to direct sequencing and is much more rapid and cost effective than cloning the PCR products and sequencing the clones.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A method for detecting a variation in a nucleic acid molecule said method comprising:
   (a) providing the nucleic acid;
   (b) transforming the nucleic acid into one or more single stranded nucleic acid spatial conformer(s);
   (c) separating the conformer(s) under native conditions;
   (d) changing one or more conditions of the separation at least twice during the separation wherein the change imparts a conformation change in the conformer(s);
   (e) detecting the mobility pattern of the conformer(s); and
   (f) comparing the mobility pattern of the conformers to a mobility pattern of a second nucleic acid conformer so as to thereby detect a variation between the nucleic acid molecules,
   wherein when the condition is temperature, the temperature is lowered during the separation.

2. The method of claim 1, wherein the variation is a single base difference.

3. The method of claim 2, wherein said single base difference is a single nucleotide polymorphism.

4. The method of claim 2, wherein said single base difference is a mutation.

5. The method of claim 1, wherein said nucleic acid molecule comprises double stranded DNA.

6. The method of claim 1, wherein said nucleic acid molecule comprises RNA.

7. The method of claim 1, wherein said nucleic acid is obtained from a sample selected from the group consisting of a bacterium, virus, fungus, protozoan, plant, animal or human.

8. The method of claim 7, wherein said nucleic acid is obtained from a human source.

9. The method of claim 8, wherein said nucleic acid is obtained from a sample selected from the group consisting of a cell, hair, tissue, blood, urine, semen, saliva, plasma, serum, amniotic fluid or mucosa.

10. The method of claim 1, wherein said nucleic acid is provided by PCR.

11. The method of claim 1, wherein said nucleic acid is provided by LCR.

12. The method of claim 1, wherein said nucleic acid is provided by direct cloning.

13. The method of claim 1, wherein said transformation of said nucleic acid comprises subjecting said nucleic acid to physical, chemical, or enzymatic means or a combination thereof, wherein the secondary structure of said nucleic acid is disrupted.

14. The method of claim 13, wherein said physical, chemical, or enzymatic means are selected from the group consisting of low pH, high pH, high temperature, low salt concentrations, urea or formamide.

15. The method of claim 14, wherein said transformation comprises heating said nucleic acid to about 94° C.

16. The method of claim 15, further comprising treating said nucleic acid with a substance selected from the group consisting of formamide or urea.

17. The method of claim 1, wherein said separation step is selected from the group consisting of polyacrylamide gel electrophoresis, capillary electrophoresis, agarose gel electrophoresis, or chromatography.

18. The method of claim 17, wherein said separation step is polyacrylamide gel electrophoresis.

19. The method of claim 1, wherein said condition is selected from the group consisting of physical or chemical conditions, or any combination thereof.

20. The method of claim 19, wherein said condition is a physical condition.

21. The method of claim 20, wherein said physical condition is temperature.

22. The method of claim 19, wherein said condition is a chemical condition.

23. The method of claim 22, wherein said chemical condition is selected from the group consisting of ionic strength and pH.

24. The method of claim 1, wherein the step of changing the condition during said separation changes the total energy of said single stranded nucleic acid spatial conformer.

25. The method of claim 1, wherein said nucleic acid molecule contains a fluorescent label.

26. The method of claim 1, wherein said nucleic acid contains an electromagnetic label.

27. The method of claim 25, further comprising detection of said fluorescent label.

28. The method of claim 26, further comprising detection of said electromagnetic label.

29. The method of claim 1, wherein said detection is by silver staining.

30. The method of claim 1, wherein the second conformer is a wild-type sequence.

31. The method of claim 1, wherein the second conformer is a mutant sequence.

32. The method of claim 1, wherein the second conformer contains a single nucleotide polymorphism.

33. The method of claim 1, further comprising:
(a) isolating the nucleic acid conformer(s); and
(b) determining the nucleic acid sequence of said conformer(s).

34. The method of claim 33, wherein said isolation is by electro-elution.

35. A method for detecting the presence of different sequence variants in a population of nucleic acid molecules obtained from one organism said method comprising:
(a) providing the population of nucleic acid molecules;
(b) transforming the nucleic acid molecules into one or more single stranded nucleic acid spatial conformer(s);
(c) separating the conformer(s) under native conditions;
(d) changing one or more conditions of the separation at least twice during the separation wherein the change imparts a conformation change in the conformer(s);
(e) detecting the mobility pattern of the conformer(s); and
(f) comparing the mobility pattern of the conformers so as to thereby detect different sequence variants in the population of nucleic acid molecules,
wherein when the condition is temperature, the temperature is lowered during the separation.

36. The method of claim 35, further comprising:
(a) isolating said conformer(s); and
(c) determining the nucleic acid sequence of said conformer(s).

37. The method of claim 36, wherein said isolation is by electro-elution.

38. The method of claim 35, wherein said population is derived from more than one individual.

39. The method of claim 38, wherein said individuals are afflicted or are at risk of developing a genetic disease or condition.

40. A method for detecting a variation in a nucleic acid molecule, the method comprising:
(a) transforming the nucleic acid into one or more single stranded nucleic acid spatial conformer(s);
(b) separating the conformer(s) under native conditions;
(c) lowering the temperature of the separation at least once during the separation wherein the temperature change imparts a conformation change in the conformer(s);
(d) detecting the mobility pattern of the conformer(s); and
(e) comparing the mobility pattern of the conformers to a mobility pattern of a second nucleic acid conformer so as to thereby detect a variation between the nucleic acid molecules.

41. The method of claim 40, wherein the variation is a single base difference.

42. The method of claim 41, wherein the single base difference is a single nucleotide polymorphism.

43. The method of claim 41, wherein the single base difference is a mutation.

44. The method of claim 40, wherein the nucleic acid molecule comprises double stranded DNA.

45. The method of claim 40, wherein the nucleic acid molecule comprises RNA.

46. The method of claim 40, wherein the nucleic acid is obtained from a sample selected from the group consisting of a bacterium, virus, fungus, protozoan, plant, animal or human.

47. The method of claim 40, wherein the nucleic acid is obtained from a human source.

48. The method of claim 47, wherein the nucleic acid is obtained from a sample selected from the group consisting of a cell, hair, tissue, blood, urine, semen, saliva, plasma, serum, amniotic fluid or mucosa.

49. The method of claim 40, wherein the nucleic acid is provided by PCR.

50. The method of claim 40, wherein the nucleic acid is provided by LCR.

51. The method of claim 40, wherein the nucleic acid is provided by direct cloning.

52. The method of claim 40, wherein the transformation of the nucleic acid comprises subjecting the nucleic acid to physical, chemical, or enzymatic means or a combination thereof, wherein the secondary structure of the nucleic acid is disrupted.

53. The method of claim 52, wherein the physical, chemical, or enzymatic means are selected from the group consisting of low pH, high pH, high temperature, low salt concentrations, urea or formamide.

54. The method of claim 53, wherein the transformation comprises heating the nucleic acid to about 94° C.

55. The method of claim 54, further comprising treating the nucleic acid with a substance selected from the group consisting of formamide or urea.

56. The method of claim 40, wherein the separation step is selected from the group consisting of polyacrylamide gel electrophoresis, capillary electrophoresis, agarose gel electrophoresis, or chromatography.

57. The method of claim 56, wherein the separation step is polyacrylamide gel electrophoresis.

58. The method of claim 40, wherein the nucleic acid molecule contains a fluorescent label or an electromagnetic label.

59. The method of claim 40, wherein the second conformer is a wild-type sequence or a mutant sequence.

60. The method of claim 40, wherein the second conformer contains a single nucleotide polymorphism.

61. The method of claim 40, further comprising:
isolating the nucleic acid conformer(s); and
determining the nucleic acid sequence of the conformer(s).

62. The method of claim 40, wherein the isolation is by electro-elution.

* * * * *